(12) United States Patent
Bonfanti et al.

(10) Patent No.: US 7,355,051 B2
(45) Date of Patent: Apr. 8, 2008

(54) PIPERDINE-AMINO-BENZIMIDAZOLE DERIVATIVES AS INHIBITORS OF RESPIRATORY SYNCYTIAL VIRUS REPLICATION

(75) Inventors: Jean-François Bonfanti, Andé (FR); Koenraad Jozef Lodewijk Andries, Beerse (BE); Frans Eduard Janssens, Bonheiden (BE); François Maria Sommen, Wortel (BE); Jerôme Emile Georges Guillemont, Andé (FR); Jean Fernand Armand Lacrampe, Le Mesnil-Esnard (FR)

(73) Assignee: Tibotec Pharmaceuticals, County Cork (IE)

( * ) Notice: Subject to any disclaimer, the term of this patent is extended or adjusted under 35 U.S.C. 154(b) by 0 days.

(21) Appl. No.: 10/596,519

(22) PCT Filed: Dec. 20, 2004

(86) PCT No.: PCT/EP2004/053606

§ 371 (c)(1),
(2), (4) Date: Jun. 15, 2006

(87) PCT Pub. No.: WO2005/058873

PCT Pub. Date: Jun. 30, 2005

(65) Prior Publication Data

US 2007/0093659 A1    Apr. 26, 2007

Related U.S. Application Data

(60) Provisional application No. 60/566,835, filed on Apr. 30, 2004.

(30) Foreign Application Priority Data

Dec. 18, 2003  (EP)  .................. 03104802

(51) Int. Cl.
C07D 401/106    (2006.01)
(52) U.S. Cl. .................................. 548/306.1
(58) Field of Classification Search ............. 548/306.1
See application file for complete search history.

(56) References Cited

U.S. PATENT DOCUMENTS 4,219,559 A * 8/1980 Janssens et al. ............ 514/322

FOREIGN PATENT DOCUMENTS

| EP | 0005318 B1 | 11/1979 |
|---|---|---|
| EP | 0099139 B1 | 6/1983 |
| EP | 0145037 B1 | 9/1984 |
| WO | WO 92/01687 A1 | 2/1992 |
| WO | WO 01/00611 A1 | 1/2001 |
| WO | WO-01-00611 A1 * | 1/2001 |
| WO | WO 01/00612 A1 | 1/2001 |
| WO | WO 01/00615 A1 | 1/2001 |

OTHER PUBLICATIONS

Janssens et al. Journal of Medicinal Chemistry, 1985, 28, 1934-1943; p. 1939, Example 87.*
International Search Report, International Application No. PCT/EP2004/053606, Date of Mailing of International Search Report, Apr. 15, 2005.
Benet, et al., "Pharmacokinetics: The Dynamics of Drug Absorption, Distribution, and Elimination.", *Goodman and Gilman's The Pharmacological Basis of Therapeutics*, Eighth Edition, pp. 13-20, McGraw-Hill Inc.
Janssens, F. et al., "New Antihistamine N-Heterocyclic 4-Piperidinamines.2. Synthesis and Antihistaminic Activity of 1-(4-Fluorophenyl)-1H-Benzimidazol-2-Amines.", *Journal of Medicinal Chemistry*, Dec. 1985, vol. 28, No. 121, pp. 1934-1943, American Chemical Society, Washington, US, XP000881979.

* cited by examiner

*Primary Examiner*—D. Margaret Seaman
*Assistant Examiner*—Nizal S. Chandrakumar

(57) ABSTRACT

The present invention concerns piperidine-amino-benzimidazoles having inhibitory activity on the replication of the respiratory syncytial virus and having the formula  (I)

their prodrugs, N-oxides, addition salts, quaternary amines, metal complexes and stereochemically isomeric forms wherein Q is $C_{1-6}$alkyl optionally substituted with trifluoromethyl, $C_{3-7}$cycloalkyl, $Ar^2$, hydroxy, $C_{1-4}$alkoxy, $C_{1-4}$alkylthio, $Ar^2$-oxy-, $Ar^2$-thio-, $Ar^2(CH_2)_n$oxy, $Ar^2(CH_2)_n$ thio, hydroxycarbonyl, aminocarbonyl, $C_{1-4}$alkylcarbonyl, $Ar^2$carbonyl, $C_{1-4}$alkoxycarbonyl, $Ar^2(CH_2)_n$carbonyl, aminocarbonyloxy, $C_{1-4}$alkylcarbonyloxy, $Ar^2$carbonyloxy, $Ar^2(CH_2)_n$carbonyloxy, $C_{1-4}$alkoxy-carbonyl($CH_2)_n$oxy, mono- or di($C_{1-4}$alkyl)aminocarbonyl, mono- or di($C_{1-4}$ alkyl)-aminocarbonyloxy, aminosulfonyl, mono- or di($C_{1-4}$ alkyl)aminosulfonyl or a heterocycles selected from the group consisting of pyrrolidinyl, pyrrolyl, dihydropyrrolyl, imidazolyl, triazolyl, piperidinyl, homopiperidinyl, piperazinyl, morpholinyl, thiomorpholinyl, 1-oxo-thiomorpholinyl, 1,1-dioxothiomorpholinyl, pyridyl and tetrahydropyridyl, wherein each of said heterocycle may optionally be substituted with oxo or $C_{1-6}$alkyl; G is a direct bond or optionally substituted $C_{1-10}$alkanediyl; $R^1$ is $Ar^1$ or a monocyclic or bicyclic heterocycle; one of $R^{2a}$ and $R^{3a}$ is $C_{1-6}$alkyl and the other one of $R^{2a}$ and $R^{3a}$ is hydrogen; in case $R^{2a}$ is different from hydrogen then $R^{2b}$ is hydrogen or $C_{1-6}$alkyl, and $R^{3b}$ is hydrogen; in case $R^{3a}$ is different from hydrogen then $R^{3b}$ is hydrogen or $C_{1-6}$alkyl, and $R^{2b}$ is hydrogen; t is 1, 2 or 3; $Ar^1$ is phenyl or substituted phenyl; and $Ar^2$ is phenyl or substituted phenyl. It further concerns their preparation and compositions comprising them, as well as their use as a medicine.

8 Claims, No Drawings

PIPERDINE-AMINO-BENZIMIDAZOLE DERIVATIVES AS INHIBITORS OF RESPIRATORY SYNCYTIAL VIRUS REPLICATION

CROSS REFERENCE TO RELATED APPLICATIONS

This application is the national stage of PCT Application No. PCT/EP2004/053606, filed Dec. 20, 2004, which application claims priority from European Patent Application No. 03104802.8, filed 18 Dec. 2003 and U.S. provisional Patent Application No. 60/566,835, filed 30 Apr. 2004, the entire disclosures of which are hereby incorporated in their entirely.

The present invention is concerned with piperidine-amino-benzimidazole derivatives having antiviral activity, in particular, having an inhibitory activity on the replication of the respiratory syncytial virus (RSV). It further concerns the preparation thereof and compositions comprising these compounds.

Human RSV or Respiratory Syncytial Virus is a large RNA virus, member of the family of Paramyxoviridae, subfamily pneumoviridae together with bovine RSV virus. Human RSV is responsible for a spectrum of respiratory tract diseases in people of all ages throughout the world. It is the major cause of lower respiratory tract illness during infancy and childhood. Over half of all infants encounter RSV in their first year of life, and almost all within their first two years. The infection in young children can cause lung damage that persists for years and may contribute to chronic lung disease in later life (chronic wheezing, asthma). Older children and adults often suffer from a (bad) common cold upon RSV infection. In old age, susceptibility again increases, and RSV has been implicated in a number of outbreaks of pneumonia in the aged resulting in significant mortality.

Infection with a virus from a given subgroup does not protect against a subsequent infection with an RSV isolate from the same subgroup in the following winter season. Re-infection with RSV is thus common, despite the existence of only two subtypes, A and B.

Today only three drugs have been approved for use against RSV infection. A first one is ribavirin, a nucleoside analogue, provides an aerosol treatment for serious RSV infection in hospitalized children. The aerosol route of administration, the toxicity (risk of teratogenicity), the cost and the highly variable efficacy limit its use. The other two drugs, RespiGam® and palivizumab, polyclonal and monoclonal antibody immunostimulants, are intended to be used in a preventive way.

Other attempts to develop a safe and effective RSV vaccine have all met with failure thus far. Inactivated vaccines failed to protect against disease, and in fact in some cases enhanced disease during subsequent infection. Life attenuated vaccines have been tried with limited success. Clearly there is a need for an efficacious non-toxic and easy to administer drug against RSV replication.

Several series of benzimidazolyl and imidazopyridinyl piperidines have been described in patents, patent applications and publications of janssen Pharmaceutica N. V. as compounds possessing antihistaminic properties. See for example EP-A-5 318, EP-A-99 139, EP-A-145 037, WO-92/01687, Janssens F. et al. in Journal of Medicinal Chemistry, Am. Chem. Soc., Vol. 28, no. 12, pp. 1934-1943 (1985).

Benzimidazoles and imidazopyridines as inhibitors of RSV replication have been described in WO 01/00611, WO 01/00612 and WO 01/00615.

The present invention concerns inhibitors of RSV replication, which can be represented by formula (I)

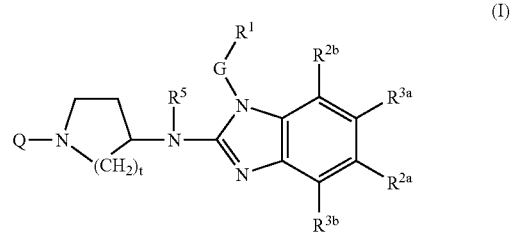

their prodrugs, N-oxides, addition salts, quaternary amines, metal complexes and stereochemically isomeric forms wherein Q is $C_{1-6}$alkyl optionally substituted with one or more substituents each independently selected from the group consisting of trifluoromethyl, $C_{3-7}$cycloalkyl, $Ar^2$, hydroxy, $C_{1-4}$alkoxy, $C_{1-4}$alkylthio, $Ar^2$-oxy-, $Ar^2$-thio-, $Ar^2(CH_2)_n$oxy, $Ar^2(CH_2)_n$thio, hydroxycarbonyl, aminocarbonyl, $C_{1-4}$alkylcarbonyl, $Ar^2$carbonyl, $C_{1-4}$alkoxycarbonyl, $Ar^2(CH_2)_n$carbonyl, aminocarbonyloxy, $C_{1-4}$alkylcarbonyl-oxy, $Ar^2$carbonyloxy, $Ar^2(CH_2)_n$carbonyloxy, $C_{1-4}$alkoxycarbonyl$(CH_2)_n$oxy, mono- or di($C_{1-4}$alkyl)aminocarbonyl, mono- or di($C_{1-4}$alkyl)aminocarbonyloxy, aminosulfonyl, mono- or di($C_{1-4}$alkyl)aminosulfonyl or a heterocycle selected from the group consisting of pyrrolidinyl, pyrrolyl, dihydropyrrolyl, imidazolyl, triazolyl, piperidinyl, homopiperidinyl, piperazinyl, pyridyl and tetrahydro-pyridyl, wherein each of said heterocycle may optionally be substituted with oxo or $C_{1-6}$alkyl; or Q is $C_{1-6}$alkyl substituted with two substituents wherein one substituent is selected from the group consisting of amino, mono- and di$C_{1-4}$alkylamino and $Ar^2$-$C_{1-4}$alkylamino and the other substituent is selected from the group consisting of carboxyl, $C_{1-6}$alkyloxycarbonyl, $Ar^2$-$C_{1-4}$alkyloxycarbonyl, aminocarbonyl and aminosulfonyl;

G is a direct bond or $C_{1-10}$alkanediyl optionally substituted with one or more substituents independently selected from the group consisting of hydroxy, $C_{1-6}$alkyloxy, $Ar^1C_{1-6}$alkyloxy, $C_{1-6}$alkylthio, $Ar^1C_{1-6}$alkylthio, $HO(-CH_2-CH_2-O)_n-$, $C_{1-16}$alkyloxy$(-CH_2-CH_2-O)_n-$ and $Ar^1C_{1-6}$alkyloxy$(-CH_2-CH_2-O)_n-$;

$R^1$ is $Ar^1$ or a monocyclic or bicyclic heterocycle being selected from piperidinyl, piperazinyl, pyridyl, pyrazinyl, pyridazinyl, pyrimidinyl, furanyl, tetrahydro-furanyl, thienyl, pyrrolyl, thiazolyl, oxazolyl, imidazolyl, isothiazolyl, pyrazolyl, isoxazolyl, oxadiazolyl, quinolinyl, quinoxalinyl, benzofuranyl, benzothienyl, benzimidazolyl, benzoxazolyl, benzthiazolyl, pyridopyridyl, naphthiridinyl, 1H-imidazo[4,5-b]pyridinyl, 3H-imidazo[4,5-b]pyridinyl, imidazo[1,2-a]-pyridinyl, 2,3-dihydro-1,4-dioxino[2,3-b]pyridyl or a radical of formula (c-1)

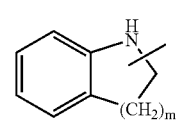

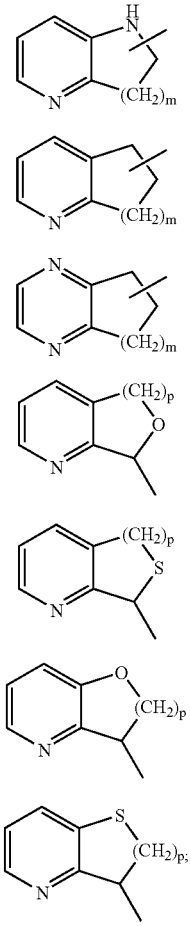

wherein each of said monocyclic or bicyclic heterocycles may optionally be substituted with 1 or where possible more, such as 2, 3, 4 or 5, substituents individually selected from the group of substituents consisting of halo, hydroxy, amino, cyano, carboxyl, $C_{1-6}$alkyl, $C_{1-6}$alkyloxy, $C_{1-6}$alkylthio, $C_{1-6}$alkyloxy$C_{1-6}$alkyl, $Ar^1$, $Ar^1C_{1-6}$alkyl, $Ar^1C_{1-6}$alkyloxy, hydroxy$C_{1-6}$alkyl, mono- or di($C_{1-6}$alkyl)amino, mono- or di($C_{1-6}$alkyl)amino$C_{1-6}$alkyl, polyhalo$C_{1-6}$alkyl, $C_{1-6}$alkylcarbonylamino, $C_{1-6}$alkyl-$SO_2$—$NR^{4a}$—, $Ar^1$—$SO_2$—$NR^{4a}$—, $C_{1-6}$alkyloxycarbonyl, —C(=O)—$NR^{4a}R^{4b}$, HO(—$CH_2$—$CH_2$—O)$_n$—, halo(—$CH_2$—$CH_2$—O)$_n$—, $C_{1-6}$alkyloxy(—$CH_2$—$CH_2$—O)$_n$—, $Ar^1C_{1-6}$alkyloxy(—$CH_2$—$CH_2$—O)$_n$— and mono- or di($C_{1-6}$alkyl)amino(—$CH_2$—$CH_2$—O)$_n$—;

each n independently is 1, 2, 3 or 4;

one of $R^{2a}$ and $R^{3a}$ is $C_{1-6}$alkyl and the other one of $R^{2a}$ and $R^{3a}$ is hydrogen;

in case $R^{2a}$ is different from hydrogen then $R^{2b}$ is hydrogen or $C_{1-6}$alkyl, and $R^{1b}$ is hydrogen;

in case $R^{3a}$ is different from hydrogen then $R^{3b}$ is hydrogen or $C_{1-6}$alkyl, and $R^{2b}$ is hydrogen; or $R^{3b}$ is $C_{1-6}$alkyl; and $R^{3a}$, $R^{2a}$, $R^{2b}$ all are hydrogen; or $R^{2b}$ is $C_{1-6}$alkyl; and $R^{3a}$, $R^{2a}$, $R^{3b}$ all are hydrogen;

$R^{4a}$ and $R^{4b}$ can be the same or can be different relative to one another, and are each independently hydrogen or $C_{1-6}$alkyl; or $R^{4a}$ and $R^{4b}$ taken together may form a bivalent radical of formula —(CH$_2$)$_n$—;

$R^5$ is hydrogen or $C_{1-6}$alkyl;

m is 1 or 2;

p is 1 or 2;

s is 4 or 5;

t is 1, 2 or 3;

$Ar^1$ is phenyl or phenyl substituted with 1 or more, such as 2, 3 or 4, substituents selected from halo, hydroxy, $C_{1-6}$alkyl, hydroxy$C_{1-6}$alkyl, polyhalo$C_{1-6}$alkyl, and $C_{1-6}$alkyloxy;

$Ar^2$ is phenyl or phenyl substituted with 1 or more, such as 2, 3 or 4, substituents selected from the group consisting of halo, hydroxy, amino, cyano, $C_{1-6}$alkyl, hydroxy$C_{1-6}$alkyl, polyhalo$C_{1-16}$alkyl, amino$C_{1-16}$alkyl, $C_{1-16}$alkyloxy, aminosulfonyl, aminocarbonyl, hydroxycarbonyl, $C_{1-14}$alkylcarbonyl, mono- or di($C_{1-4}$alkyl)amino, mono- or di($C_{1-4}$alkyl)aminocarbonyl, mono- or di($C_{1-4}$alkyl)aminosulfonyl, mono- or di($C_{1-4}$alkyl)amino$C_{1-6}$alkyl and $C_{1-4}$alkoxycarbonyl.

The invention further relates to the use of a compound of formula (I), or a prodrug, N-oxide, addition salt, quaternary amine, metal complex and stereochemically isomeric form thereof, for the manufacture of a medicament for inhibiting RSV replication. Or the invention relates to a method of inhibiting RSV replication in a warm-blooded animal said method comprising the administration of an effective amount of a compound of formula (I), or a prodrug, N-oxide, addition salt, quaternary amine, metal complex and stereochemically isomeric form thereof.

In a further aspect, this invention relates to novel compounds of formula (I) as well as methods for preparing these compounds.

The term 'prodrug' as used throughout this text means the pharmacologically acceptable derivatives, e.g. esters and amides, such that the resulting biotransformation product of the derivative is the active drug as defined in the compounds of formula (I). The reference by Goodman and Gilman (The Pharmacological Basis of Therapeutics, 8$^{th}$ ed., McGraw-Hill, Int. Ed. 1992, "Biotransformation of Drugs", p. 13-15) describing prodrugs generally, is hereby incorporated. Prodrugs are characterized by a good aqueous solubility and bioavailability, and are readily metabolized into the active inhibitors in vivo.

The terms '$C_{1-6}$alkyl optionally substituted with one or more substituents' such as used in the definition of Q, or '$C_{1-10}$alkanediyl optionally substituted with one or more substituents' as used in the definition of G are meant to comprise $C_{1-6}$alkyl radicals respectively $C_{1-10}$alkanediyl radicals having no, one, two or more substituents, for example no, one, two, three, four, five or six substituents, in particular no, one, two or three substituents, further in particular no, one or two substituents. The upper limit of the number of substituents is determined by the number of hydrogen atoms that can be replaced as well as by the general properties of the substituents such as their bulkiness, these properties allowing the skilled person to determine said upper limit.

As used in the foregoing and hereinafter, 'polyhalo$C_{1-6}$alkyl' as a group or part of a group, e.g. in polyhalo$C_{1-6}$alkyloxy, is defined as mono- or polyhalo substituted $C_{1-6}$alkyl, in particular $C_{1-6}$alkyl substituted with up to one, two, three, four, five, six, or more halo atoms, such as methyl or ethyl with one or more fluoro atoms, for example, difluoromethyl, trifluoromethyl, trifluoroethyl. Also included are perfluoro $C_{1-6}$alkyl groups, which are $C_{1-6}$alkyl groups wherein all hydrogen atoms are replaced by fluoro atoms, e.g. pentafluoroethyl. In case more than one halogen atom is attached to an alkyl group within the definition of polyhalo$C_{1-4}$alkyl, the halogen atoms may be the same or different.

Each of the monocyclic or bicyclic heterocycles in the definition of $R^1$ may optionally be substituted with 1 or where possible more substituents, such as 2, 3, 4 or 5, substituents. In particular, said heterocycles may optionally be substituted with up to 4, up to 3, up to 2 substituents, or up to 1 substituent.

Each $Ar^1$ or $Ar^2$ may be unsubstituted phenyl or phenyl substituted with 1 or more substituents, such as 5 or 4 substituents or, which is preferred, up to 3 substituents, or up to two substituents, or with one substituent.

A hydroxy$C_{1-6}$alkyl group when substituted on an oxygen atom or a nitrogen atom preferably is a hydroxy$C_{2-6}$alkyl group wherein the hydroxy group and the oxygen or nitrogen is separated by at least two carbon atoms.

As used herein $C_{1-3}$alkyl as a group or part of a group defines straight or branched chain saturated hydrocarbon radicals having from 1 to 3 carbon atoms such as methyl, ethyl, propyl, 1-methylethyl and the like; $C_{1-4}$alkyl as a group or part of a group defines straight or branched chain saturated hydrocarbon radicals having from 1 to 4 carbon atoms such as the group defined for $C_{1-3}$alkyl and butyl and the like; $C_{2-4}$alkyl as a group or part of a group defines straight or branched chain saturated hydrocarbon radicals having from 2 to 4 carbon atoms such as ethyl, propyl, 1-methylethyl, butyl and the like; $C_{1-6}$alkyl as a group or part of a group defines straight or branched chain saturated hydrocarbon radicals having from 1 to 6 carbon atoms such as the groups defined for $C_{1-4}$alkyl and pentyl, hexyl, 2-methylbutyl and the like; $C_{1-9}$alkyl as a group or part of a group defines straight or branched chain saturated hydrocarbon radicals having from 1 to 9 carbon atoms such as the groups defined for $C_{1-6}$alkyl and heptyl, octyl, nonyl, 2-methylhexyl, 2-methylheptyl and the like; $C_{1-10}$alkyl as a group or part of a group defines straight or branched chain saturated hydrocarbon radicals having from 1 to 10 carbon atoms such as the groups defined for $C_{1-9}$alkyl and decyl, 2-methylnonyl and the like.

$C_{3-7}$cycloalkyl is generic to cyclopropyl, cyclobutyl, cyclopentyl, cyclohexyl and cycloheptyl.

$C_{2-5}$ alkanediyl defines bivalent straight and branched chain saturated hydrocarbon radicals having from 2 to 5 carbon atoms such as, for example, 1,2-ethanediyl, 1,3-propanediyl, 1,4-butanediyl, 1,2-propanediyl, 2,3-butanediyl, 1,5-pentanediyl and the like, $C_{1-4}$ alkanediyl defines bivalent straight and branched chain saturated hydrocarbon radicals having from 1 to 4 carbon atoms such as, for example, methylene, 1,2-ethanediyl, 1,3-propanediyl, 1,4-butanediyl and the like; $C_{1-6}$ alkanediyl is meant to include $C_{1-4}$alkanediyl and the higher homologues thereof having from 5 to 6 carbon atoms such as, for example, 1,5-pentanediyl, 1,6-hexanediyl and the like; $C_{1-10}$alkanediyl is meant to include $C_{1-6}$alkanediyl and the higher homologues thereof having from 7 to 10 carbon atoms such as, for example, 1,7-heptanediyl, 1,8-octanediyl, 1,9-nonanediyl, 1,10-decanediyl and the like.

As used herein before, the term (═O) forms a carbonyl moiety when attached to a carbon atom, a sulfoxide moiety when attached to a sulfur atom and a sulfonyl moiety when two of said terms are attached to a sulfur atom. The term (═N—OH) forms a hydroxylimine moiety when attached to a carbon atom.

The term 'halo' is generic to fluoro, chloro, bromo and iodo.

It should be noted that the radical positions on any molecular moiety used in the definitions may be anywhere on such moiety as long as it is chemically stable.

Radicals used in the definitions of the variables include all possible isomers unless otherwise indicated. For instance pyridyl includes 2-pyridyl, 3-pyridyl and 4-pyridyl; pentyl includes 1-pentyl, 2-pentyl and 3-pentyl.

When any variable occurs more than one time in any constituent, each definition is independent.

Whenever used hereinafter, the terms 'compounds of formula (I)', or 'the present compounds' or similar terms are meant to include the compounds of general formula (I), their prodrugs, N-oxides, addition salts, quaternary amines, metal complexes and stereochemically isomeric forms. An interesting subgroup of the compounds of formula (I) or any subgroup thereof are the N-oxides, salts and all the stereoisomeric forms of the compounds of formula (I).

It will be appreciated that some of the compounds of formula (I) may contain one or more centers of chirality and exist as stereochemically isomeric forms.

The term "stereochemically isomeric forms" as used hereinbefore defines all the possible compounds made up of the same atoms bonded by the same sequence of bonds but having different three-dimensional structures which are not interchangeable, which the compounds of formula (I) may possess.

Unless otherwise mentioned or indicated, the chemical designation of a compound encompasses the mixture of all possible stereochemically isomeric forms which said compound may possess. Said mixture may contain all diastereomers and/or enantiomers of the basic molecular structure of said compound. All stereochemically isomeric forms of the compounds of the present invention both in pure form or in admixture with each other are intended to be embraced within the scope of the present invention.

Pure stereoisomeric forms of the compounds and intermediates as mentioned herein are defined as isomers substantially free of other enantiomeric or diastereomeric forms of the same basic molecular structure of said compounds or intermediates. In particular, the term 'stereoisomerically pure' concerns compounds or intermediates having a stereoisomeric excess of at least 80% (i.e. minimum 90% of one isomer and maximum 10% of the other possible isomers) up to a stereoisomeric excess of 100% (i.e. 100% of one isomer and none of the other), more in particular, compounds or intermediates having a stereoisomeric excess of 90% up to 100%, even more in particular having a stereoisomeric excess of 94% up to 100% and most in particular having a stereoisomeric excess of 97% up to 100%. The terms 'enantiomerically pure' and 'diastereomerically pure' should be understood in a similar way, but then having regard to the enantiomeric excess, respectively the diastereomeric excess of the mixture in question.

Pure stereoisomeric forms of the compounds and intermediates of this invention may be obtained by the application of art-known procedures. For instance, enantiomers may be separated from each other by the selective crystallization of their diastereomeric salts with optically active acids or bases. Examples thereof are tartaric acid, dibenzoyltartaric acid, ditoluoyltartaric acid and camphosulfonic acid. Alternatively, enantiomers may be separated by chromatographic techniques using chiral stationary phases. Said pure stereochemically isomeric forms may also be derived from the corresponding pure stereochemically isomeric forms of the appropriate starting materials, provided that the reaction occurs stereospecifically. Preferably, if a specific stereoisomer is desired, said compound will be synthesized by stereospecific methods of preparation. These methods will advantageously employ enantiomerically pure starting materials.

The diastereomeric racemates of formula (I) can be obtained separately by conventional methods. Appropriate physical separation methods that may advantageously be employed are, for example, selective crystallization and chromatography, e.g. column chromatography.

For some of the compounds of formula (I), their prodrugs, N-oxides, salts, solvates, quaternary amines, or metal complexes and the intermediates used in the preparation thereof, the absolute stereochemical configuration was not experimentally determined. A person skilled in the art is able to determine the absolute configuration of such compounds using art-known methods such as, for example, X-ray diffraction.

The present invention is also intended to include all isotopes of atoms occurring on the present compounds. Isotopes include those atoms having the same atomic number but different mass numbers. By way of general example and without limitation, isotopes of hydrogen include tritium and deuterium. Isotopes of carbon include C-13 and C-14.

For therapeutic use, salts of the compounds of formula (I) are those wherein the counterion is pharmaceutically acceptable. However, salts of acids and bases, which are non-pharmaceutically acceptable may also find use, for example, in the preparation or purification of a pharmaceutically acceptable compound. All salts, whether pharmaceutically acceptable or not are included within the ambit of the present invention.

The pharmaceutically acceptable acid and base addition salts as mentioned hereinabove are meant to comprise the therapeutically active non-toxic acid and base addition salt forms which the compounds of formula (I) are able to form. The pharmaceutically acceptable acid addition salts can conveniently be obtained by treating the base form with such appropriate acid. Appropriate acids comprise, for example, inorganic acids such as hydrohalic acids, e.g. hydrochloric or hydrobromic acid, sulfuric, nitric, phosphoric and the like acids; or organic acids such as, for example, acetic, propanoic, hydroxyacetic, lactic, pyruvic, oxalic (i.e. ethanedioic), malonic, succinic (i.e. butanedioic acid), maleic, fumaric, malic (i.e. hydroxybutanedioic acid), tartaric, citric, methanesulfonic, ethanesulfonic, benzenesulfonic, p-toluenesulfonic, cyclamic, salicylic, p-aminosalicylic, pamoic and the like acids.

Conversely said salt forms can be converted by treatment with an appropriate base into the free base form.

The compounds of formula (I) containing an acidic proton may also be converted into their non-toxic metal or amine addition salt forms by treatment with appropriate organic and inorganic bases. Appropriate base salt forms comprise, for example, the ammonium salts, the alkali and earth alkaline metal salts, e.g. the lithium, sodium, potassium, magnesium, calcium salts and the like, salts with organic bases, e.g. the benzathine, N-methyl-D-glucamine, hydrabamine salts, and salts with amino acids such as, for example, arginine, lysine and the like.

The term addition salt as used hereinabove also comprises the solvates which the compounds of formula (I) as well as the salts thereof, are able to form. Such solvates are for example hydrates, alcoholates and the like.

The term "quaternary amine" as used hereinbefore defines the quaternary ammonium salts which the compounds of formula (I) are able to form by reaction between a basic nitrogen of a compound of formula (I) and an appropriate quaternizing agent, such as, for example, an optionally substituted alkylhalide, arylhalide or arylalkylhalide, e.g. methyliodide or benzyliodide. Other reactants with good leaving groups may also be used, such as alkyl trifluoromethanesulfonates, alkyl methanesulfonates, and alkyl p-toluenesulfonates. A quaternary amine has a positively charged nitrogen. Pharmaceutically acceptable counterions include chloro, bromo, iodo, trifluoroacetate and acetate. The counterion of choice can be introduced using ion exchange resins.

The N-oxide forms of the present compounds are meant to comprise the compounds of formula (I) wherein one or several nitrogen atoms are oxidized to the so-called N-oxide.

It will be appreciated that the compounds of formula (I) may have metal binding, chelating, complexating properties and therefore may exist as metal complexes or metal chelates. Such metalated derivatives of the compounds of formula (I) are intended to be included within the scope of the present invention.

Some of the compounds of formula (I) may also exist in their tautomeric form. Such forms although not explicitly indicated in the above formula are intended to be included within the scope of the present invention.

One embodiment of the present invention concerns compounds of formula (I-a):

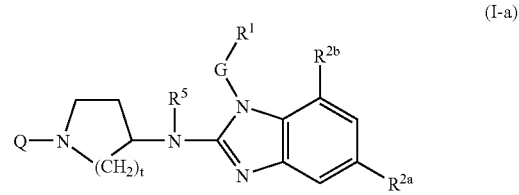

wherein Q, t, $R^5$, G and $R^1$ are as specified above in the definitions of the compounds of formula (I) or as in any of the subgroups of compounds (I) specified herein; and $R^{2a}$ is $C_{1-6}$alkyl;

$R^{2b}$ is hydrogen or $C_{1-6}$alkyl.

Another embodiment of the present invention concerns compounds of formula (I-b):

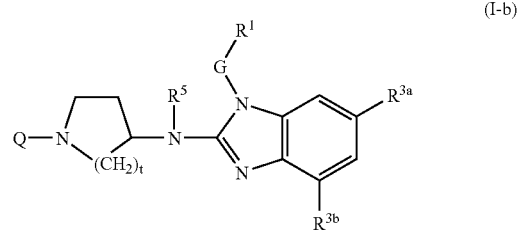

wherein Q, t, $R^5$, G and $R^1$ are as specified above in the definitions of the compounds of formula (I) or as in any of the subgroups of compounds (I) specified herein; and —$R^{3a}$ is $C_{1-6}$alkyl;

$R^{3b}$ is hydrogen or $C_{1-6}$alkyl.

Another embodiment of the present invention concerns compounds of formula (I-c):

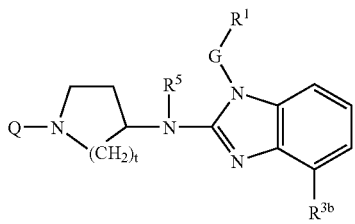

wherein Q, t, $R^5$, G and $R^1$ are as specified above in the definitions of the compounds of formula (I) or as in any of the subgroups of compounds (I) specified herein; and $R^{3b}$ is $C_{1-6}$alkyl.

Still further embodiments comprise compounds of formula (I-a), (I-b) or (I-c) wherein t=2, i.e. compounds of formulae

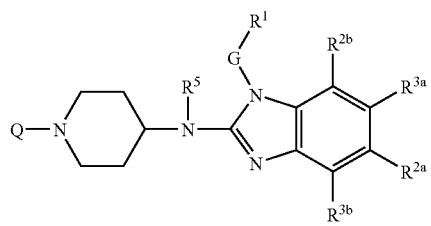

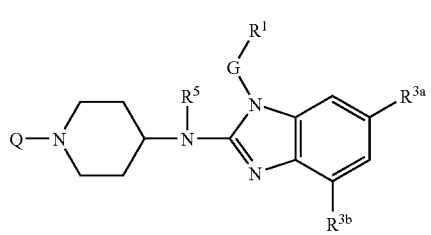

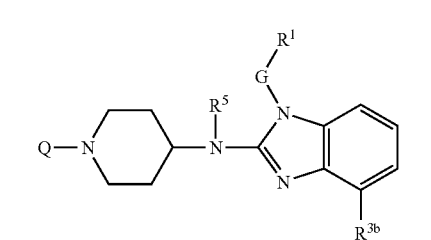

wherein Q, $R^5$, G, $R^1$, $R^{2a}$, $R^{2a}$, $R^{3a}$, $R^{3b}$ are as specified above in the definitions of the compounds of formula (I) or as in any of the subgroups of compounds (I) specified herein.

It is to be understood that the above defined subgroups of compounds of formulae (I-a), (I-b), etc. as well as any other subgroup defined herein, are meant to also comprise any prodrugs, N-oxides, addition salts, quaternary amines, metal complexes and stereochemically isomeric forms of such compounds.

Particular subgroups of the compounds of formula (I) are those compounds of formula (I), or any subgroup of compounds of formula (I) specified herein, wherein G is $C_{1-10}$alkanediyl, more in particular wherein G is methylene.

Other particular subgroups of the compounds of formula (I) are those compounds of formula (I), or any subgroup of compounds of formula (I) specified herein, wherein (a) $R^1$ is other than $Ar^1$; or wherein (b) $R^1$ is $Ar^1$ or a monocyclic heterocycle, which is as specified in the definitions of the compounds of formula (I) or any of the subgroups thereof.

Further particular subgroups of the compounds of formula (I) are those compounds of formula (I), or any subgroup of compounds of formula (I) specified herein, wherein (c) $R^1$ is pyridyl optionally substituted with 1 or 2 substituents independently selected from the group consisting of halo, hydroxy, amino, cyano, carboxyl, $C_{1-6}$alkyl, $C_{1-6}$alkyloxy, $C_{1-6}$alkylthio, $C_{1-6}$alkyloxy$C_{1-6}$alkyl, $Ar^1$, $Ar^1C_{1-6}$alkyl, $Ar^1C_{1-6}$alkyl-oxy, hydroxy$C_{1-6}$alkyl, mono- or di($C_{1-6}$alkyl)amino, mono- or di($C_{1-6}$alkyl)amino-$C_{1-16}$alkyl, polyhalo$C_{1-16}$alkyl, $C_{1-16}$alkylcarbonylamino, $C_{1-16}$alkyl-$SO_2$—$NR^{4a}$—, $Ar^1$—$SO_2$—$NR^{4a}$, $C_{1-6}$alkyloxycarbonyl, —C(=O)—$NR^{4a}R^4$, HO(—$CH_2$—$CH_2$—O)$_n$—, halo(—$CH_2$—$CH_2$—O)$_n$—, $C_{1-6}$alkyloxy(—$CH_2$—$CH_2$—O)$_n$—, $Ar^1C_{1-6}$alkyloxy(—$CH_2$—$CH_2$—O)$_n$— and mono- or di($C_{1-6}$alkyl)amino(—$CH_2$—$CH_2$—O)$_n$—; or more in particular (d) $R^1$ is pyridyl substituted with 1 or 2 substituents independently selected from the group consisting of hydroxy, $C_{1-6}$alkyl, halo, $C_{1-6}$alkyloxy, $Ar^1C_{1-6}$alkyloxy and ($C_{1-16}$alkyloxy)$C_{1-16}$alkyloxy; preferably wherein (e) $R^1$ is pyridyl substituted with 1 or 2 substituents independently selected from the group consisting of hydroxy, $C_{1-6}$alkyl, halo and $C_{1-6}$alkyloxy; or wherein (f) $R^1$ is pyridyl substituted with 1 or 2 substituents independently selected from the group consisting of hydroxy and $C_{1-6}$alkyl; more preferably wherein (g) $R^1$ is pyridyl substituted with hydroxy and $C_{1-6}$alkyl; or more preferably wherein (h) $R^1$ is pyridyl substituted with hydroxy and methyl; or wherein (i) $R^1$ is 3-hydroxy-6-methylpyrid-2-yl.

Further embodiments comprise those compounds of formula (I) or any of the subgroups of compounds of formula (I) wherein (j) $R^1$ is $Ar^1$, quinolinyl, benzimidazolyl, a radical of formula

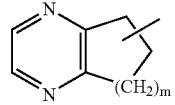

(c-4)

pyrazinyl, or pyridyl; or wherein (k) $R^1$ is $Ar^1$, quinolinyl, benzimidazolyl or a radical of formula (I-4) wherein m is 2, pyrazinyl, or pyridyl;

wherein each of the radicals in (j) and (k) may optionally be substituted with the substituents specified in the definition of the compounds of formula (I) and in particular pyridyl may be substituted as specified above in (a) to (i).

Further embodiments comprise those compounds of formula (I) or any of the subgroups of compounds of formula (I) wherein (l) $R^1$ is $Ar^1$, quinolinyl, benzimidazolyl or a radical of formula (c-4) wherein m is 2, pyrazinyl, or pyridyl, wherein each of these radicals may optionally be substituted with one, two or three radicals selected from the group consisting of halo, hydroxy, $C_{1-6}$alkyl, $C_{1-6}$alkyloxy, $Ar^1C_{1-6}$alkyloxy, ($C_{1-6}$alkyloxy)$C_{1-6}$alkyloxy; or more specifically wherein (m) $R^1$ is $Ar^1$, quinolinyl, benzimidazolyl or a radical of formula (c-4) wherein m is 2, pyrazinyl, or pyridyl, wherein each of these radicals may optionally be substituted with one, two or three radicals selected from the group consisting of halo, hydroxy, $C_{1-6}$alkyl, $C_{1-6}$alkyloxy, benzyloxy; or more specifically wherein (n) $R^1$ is phenyl optionally substituted with one, two or three radicals selected from the group consisting of halo, hydroxy, $C_{1-6}$alkyl, $C_{1-6}$alkyloxy; quinolinyl; a radical (c-4) wherein m is 2, optionally substituted with up to two radicals selected from $C_{1-6}$alkyl; benzimidazolyl optionally substituted with $C_{1-6}$alkyl; pyridyl optionally substituted with one or two radicals selected from hydroxy, halo, $C_{1-6}$alkyl, benzyloxy and $C_{1-6}$alkyloxy, pyrazinyl optionally substituted with up to three radicals selected from $C_{1-6}$alkyl; or pyridyl substituted or optionally substituted as specified above in (a)-(i); or wherein (o) $R^1$ is phenyl optionally substituted with one or two radicals selected from the group consisting of halo, hydroxy, $C_{1-6}$alkyl, $C_{1-6}$alkyloxy; or (p) $R^1$ is quinolinyl; or (q) $R^1$ is a radical (c-4) wherein m is 2, optionally substituted with up to two radicals selected from $C_{1-6}$alkyl; or (r) $R^1$ is benzimidazolyl optionally substituted with $C_{1-6}$alkyl; pyridyl optionally substituted with one or two radicals selected from hydroxy, halo, $C_{1-6}$alkyl, benzyloxy and $C_{1-6}$alkyloxy; or (s) $R^1$ is pyrazinyl optionally substituted with up to three radicals selected from $C_{1-6}$alkyl.

Preferred subgroups of compounds of formula (I) or any of the subgroups of compounds of formula (I) are those wherein G is a direct bond or methylene and $R^1$ is as specified above in (a)-(s). Further preferred are the compounds of formula (I) or any of the subgroups specified herein wherein G is a direct bond and $R^1$ is a radical (c-4), in particular wherein m is 2, optionally substituted with up to two radicals selected from $C_{1-6}$alkyl. Further preferred are the compounds of formula (I) or any of the subgroups specified herein wherein or G is methylene and $R^1$ is as specified above in (a)-(s), but is other than a radical (c-4).

Other embodiments comprise those compounds of formula (I) or any of the subgroups of compounds of formula (I) specified herein, wherein $R^5$ is hydrogen.

Further embodiments comprise those compounds of formula (I) or any of the subgroups of compounds of formula (I) specified herein, wherein (a) Q is $C_{1-6}$alkyl optionally substituted with one or more substituents each independently selected from the group consisting of trifluoromethyl, $C_{3-7}$cycloalkyl, $Ar^2$, hydroxy, $C_{1-4}$alkoxy, $C_{1-4}$alkylthio, $Ar^2$-oxy-, $Ar^2$-thio-, $Ar^2(CH_2)_n$oxy, $Ar^2(CH_2)_n$thio, hydroxycarbonyl, aminocarbonyl, $C_{1-4}$alkyl-carbonyl, $Ar^2$-carbonyl, $C_{1-4}$alkoxycarbonyl, $Ar^2(CH_2)_n$carbonyl, aminocarbonyl-oxy, $C_{1-4}$alkylcarbonyloxy, $Ar^2$-carbonyloxy, $Ar^2(CH_2)_n$carbonyloxy, $C_{1-4}$alkoxycarbonyl$(CH_2)_n$oxy, mono- or di$(C_{1-4}$alkyl)aminocarbonyl, mono- or di$(C_{1-4}$alkyl)aminocarbonyloxy, aminosulfonyl, mono- or di$(C_{1-4}$alkyl)amino-sulfonyl or a heterocycle selected from the group consisting of pyrrolidinyl, pyrrolyl, dihydropyrrolyl, imidazolyl, triazolyl, piperidinyl, homopiperidinyl, piperazinyl, pyridyl and tetrahydropyridyl, wherein each of said heterocycle may optionally be substituted with oxo or $C_{1-6}$alkyl; or in particular wherein (b) Q is $C_{1-6}$alkyl optionally substituted with one or two substituents each independently selected from the group consisting of trifluoromethyl, $C_{3-7}$cycloalkyl, $Ar^2$, hydroxy, $C_{1-4}$alkoxy, $C_{1-4}$alkylthio, $Ar^2$-oxy-, $Ar^2(CH_2)_n$oxy, hydroxycarbonyl, aminocarbonyl, $C_{1-4}$alkylcarbonyl, $C_{1-4}$alkoxycarbonyl, aminocarbonyloxy, $C_{1-4}$alkylcarbonyloxy, $Ar^2(CH_2)_n$carbonyloxy, $C_{1-4}$alkoxycarbonyl$(CH_2)_n$oxy, mono- or di$(C_{1-4}$alkyl)aminocarbonyl, aminosulfonyl, mono- or di$(C_{1-4}$alkyl)aminosulfonyl or a heterocycle selected from the group consisting of pyrrolidinyl, pyrrolyl, dihydropyrrolyl, imidazolyl, triazolyl, piperidinyl, homopiperidinyl, piperazinyl, pyridyl and tetrahydropyridyl, wherein each of said heterocycle may optionally be substituted with oxo or $C_{1-6}$alkyl; or Q is $C_{1-6}$alkyl substituted with two substituents wherein one substituent is selected from the group consisting of amino, mono- and di$C_{1-4}$alkylamino and $Ar^2$-$C_{1-4}$alkylamino and the other substituent is selected from the group consisting of carboxyl, $C_{1-6}$alkyloxycarbonyl and $Ar^2$-$C_{1-4}$alkyloxycarbonyl; or more in particular wherein (c) Q is $C_{1-6}$alkyl optionally substituted with one or two substituents each independently selected from trifluoromethyl, $C_{3-7}$cycloalkyl, $Ar^2$, hydroxy, $C_{1-14}$alkoxy, $Ar^2$-oxy-, $Ar^2(CH_2)_n$oxy, hydroxycarbonyl, aminocarbonyl, $C_{1-14}$alkylcarbonyl, $C_{1-4}$alkoxycarbonyl, aminocarbonyloxy, $Ar^2(CH_2)_n$carbonyl-oxy, $C_{1-14}$alkoxycarbonyl$(CH_2)_n$oxy, mono- or di$(C_{1-4}$alkyl)aminocarbonyl, aminosulfonyl, mono- or di$(C_{1-4}$alkyl)aminosulfonyl or a heterocycle selected from pyrrolidinyl, pyrrolyl, dihydropyrrolyl, imidazolyl, triazolyl, piperidinyl, homopiperidinyl, piperazinyl and tetrahydropyridyl, wherein each of said heterocycle may optionally be substituted with oxo or $C_{1-6}$alkyl; or Q is $C_{1-6}$alkyl substituted with two substituents wherein one substituent is selected from amino and the other substituent is selected from carboxyl and $C_{1-6}$alkyloxycarbonyl;

(d) Q is $C_{1-6}$alkyl optionally substituted with one or two substituents each independently selected from trifluoromethyl, $C_{3-7}$cycloalkyl, $Ar^2$, hydroxy, $C_{1-4}$alkoxy, hydroxycarbonyl, aminocarbonyl, $C_{1-4}$alkylcarbonyl, $Ar^2$carbonyl, $C_{1-4}$alkoxycarbonyl, aminocarbonyloxy, $Ar^2(CH_2)_n$carbonyloxy, $C_{1-4}$alkoxycarbonyl$(CH_2)_n$oxy, mono- or di$(C_{1-4}$alkyl)aminocarbonyl, aminosulfonyl, mono- or di$(C_{1-4}$alkyl)aminosulfonyl or a heterocycle selected from pyrrolidinyl, dihydropyrrolyl, imidazolyl, triazolyl, piperidinyl, homopiperidinyl, piperazinyl, pyridyl and tetrahydropyridyl, wherein each of said heterocycle may optionally be substituted with oxo or $C_{1-6}$alkyl; or Q is $C_{1-6}$alkyl substituted with two substituents wherein one substituent is selected from amino, mono- and di$C_{1-4}$alkylamino and the other substituent is selected from carboxyl and $C_{1-6}$alkyloxycarbonyl; or preferably wherein (e) Q is $C_{1-16}$alkyl optionally substituted with one or two substituents each independently selected from trifluoromethyl, $C_{3-7}$cycloalkyl, $Ar^2$, hydroxy, $C_{1-14}$alkoxy, hydroxycarbonyl, aminocarbonyl, $C_{1-14}$alkylcarbonyl, $C_{1-14}$alkoxy-carbonyl, aminocarbonyloxy, $Ar^2(CH_2)_n$carbonyloxy, $C_{1-14}$alkoxycarbonyl-$(CH_2)_n$oxy, mono- or di$(C_{1-4}$alkyl)aminocarbonyl, aminosulfonyl, mono- or di$(C_{1-4}$alkyl)aminosulfonyl or a heterocycle selected from pyrrolidinyl, dihydropyrrolyl, imidazolyl, triazolyl, piperidinyl, homopiperidinyl, pyridyl and tetrahydropyridyl; or Q is $C_{1-6}$alkyl substituted with two substituents wherein one substituent is selected from amino, mono- and di$C_{1-4}$alkylamino and the other substituent is selected from carboxyl and $C_{1-6}$alkyloxycarbonyl; or more preferably wherein (f) Q is $C_{1-6}$alkyl optionally substituted with one or two substituents each independently selected from $Ar^2$, hydroxy, hydroxycarbonyl, aminocarbonyl, $C_{1-4}$alkylcarbonyl, $C_{1-4}$alkoxycarbonyl, aminocarbonyloxy, $Ar^2(CH_2)_n$ carbonyl-oxy, $C_{1-4}$alkoxycarbonyl$(CH_2)_n$oxy, mono- or di$(C_{1-4}$alkyl)aminocarbonyl, aminosulfonyl, mono- or di$(C_{1-4}$alkyl)aminosulfonyl, pyrrolidinyl, dihydropyrrolyl, piperidinyl, homopiperidinyl, pyridyl and tetrahydropyridyl; or Q is $C_{1-6}$alkyl substituted with two substituents wherein one substituent is amino and the other substituent is selected from carboxyl and $C_{1-6}$alkyloxycarbonyl; or more preferably wherein (g) Q is $C_{1-6}$alkyl optionally substituted with one or two substituents each independently selected from aminocarbonyl, $C_{1-4}$alkoxycarbonyl, aminocarbonyloxy, $Ar^2(CH_2)_n$carbonyloxy, mono- or di($C_{1-4}$alkyl)aminocarbonyl, aminosulfonyl, mono- or di($C_{1-4}$alkyl)aminosulfonyl, pyrrolidinyl, dihydropyrrolyl, piperidinyl, homopiperidinyl and tetrahydropyridyl; or Q is $C_{1-6}$alkyl substituted with two substituents wherein one substituent is amino and the other substituent is selected from carboxyl and $C_{1-6}$alkyloxycarbonyl; or (h) Q is $C_{1-6}$alkyl optionally substituted with one or two substituents each independently selected from aminocarbonyl, $C_{1-4}$alkoxycarbonyl, aminocarbonyloxy, $Ar^2(CH_2)_n$ carbonyloxy, mono- or di($C_{1-4}$alkyl)aminocarbonyl, aminosulfonyl, mono- or di($C_{1-4}$alkyl)aminosulfonyl, pyrrolidinyl, dihydropyrrolyl, piperidinyl, homopiperidinyl and tetrahydropyridyl; or wherein (i) Q is $C_{1-6}$alkyl optionally substituted with one substituent selected from aminocarbonyl, $C_{1-4}$alkoxycarbonyl, aminocarbonyloxy, $Ar^2(CH_2)_n$carbonyloxy, mono- or di($C_{1-4}$alkyl)aminocarbonyl, aminosulfonyl, mono- or di($C_{1-4}$alkyl)-aminosulfonyl, pyrrolidinyl, dihydropyrrolyl, piperidinyl, homopiperidinyl and tetrahydropyridyl, and optionally with a second substituent which is hydroxy; or Q is $C_{1-6}$alkyl substituted with two substituents wherein one substituent is amino and the other substituent is selected from carboxyl and $C_{1-6}$alkyloxycarbonyl;

(j) Q is $C_{1-6}$alkyl optionally substituted with one substituent selected from aminocarbonyl, $C_{1-4}$alkoxycarbonyl, aminocarbonyloxy, $Ar^2(CH_2)_n$carbonyloxy, mono- or di($C_{1-4}$alkyl)aminocarbonyl, aminosulfonyl, mono- or di($C_{1-4}$alkyl)aminosulfonyl, pyrrolidinyl, dihydropyrrolyl, piperidinyl, homopiperidinyl and tetrahydropyridyl, and optionally with a second substituent which is hydroxy or Q is $C_{1-6}$alkyl substituted with two substituents wherein one substituent is amino and the other substituent is selected from carboxyl and $C_{1-6}$alkyloxycarbonyl; or wherein (k) Q is $C_{1-6}$alkyl optionally substituted with one substituent selected from aminocarbonyl, $C_{1-4}$alkoxycarbonyl, aminocarbonyloxy, $Ar^2(CH_2)_n$carbonyloxy, mono- or di($C_{1-4}$alkyl)aminocarbonyl, aminosulfonyl, mono- or di($C_{1-4}$alkyl)-aminosulfonyl, pyrrolidinyl, dihydropyrrolyl, piperidinyl, homopiperidinyl and tetrahydropyridyl, and optionally with a second substituent which is hydroxy; or wherein (l) Q is $C_{1-6}$alkyl optionally substituted with aminocarbonyl, $C_{1-4}$alkoxycarbonyl, aminocarbonyloxy, $Ar^2(CH_2)_n$ carbonyloxy, mono- or di($C_{1-4}$alkyl)aminocarbonyl, aminosulfonyl, mono- or di($C_{1-4}$alkyl)aminosulfonyl, pyrrolidinyl, dihydropyrrolyl, piperidinyl, homopiperidinyl and tetrahydropyridyl; or wherein (m) Q is $C_{1-6}$alkyl substituted with aminocarbonyl, $C_{1-4}$alkoxycarbonyl, aminocarbonyloxy, mono- or di($C_{1-4}$ alkyl)aminocarbonyl, aminosulfonyl, mono- or di($C_{1-4}$ alkyl)aminosulfonyl, pyrrolidinyl, dihydropyrrolyl, piperidinyl, homopiperidinyl or tetrahydropyridyl.

In particular, $Ar^1$ is phenyl or phenyl substituted with 1, 2, 3 substituents or with 1, 2 substituents selected from those mentioned in the definition of the compounds of formula (I) or of any subgroup thereof.

Further in particular, $Ar^2$ is phenyl or phenyl substituted with 1, 2, 3 substituents or with 1, 2 substituents selected from the group consisting of those mentioned in the definition of the compounds of formula (I) or of any subgroup thereof.

In the group of compounds of formula (I) or in any of the subgroups of compounds of formula (I):

(a) $Ar^1$ preferably is phenyl or phenyl substituted with up to 3 substituents, or with up to 2 substituents, or with one substituent, selected from halo, hydroxy, $C_{1-6}$alkyl, hydroxy$C_{1-6}$alkyl, trifluormethyl, and $C_{1-6}$alkyloxy;

(b) $Ar^1$ more preferably is phenyl or phenyl substituted with up to 3 substituents, or with up to 2 substituents, or with one substituent, selected from halo, hydroxy, $C_{1-6}$alkyl and $C_{1-6}$alkyloxy;

(c) $Ar^1$ more preferably is phenyl or phenyl substituted with up to 3 substituents, or with up to 2 substituents, or with one substituent, selected from halo and $C_{1-6}$alkyl.

Further particular subgroups of the compounds of formula (I) are those compounds of formula (I), or any subgroup of compounds of formula (I) specified herein, wherein $Ar^2$ is as defined for $Ar^1$.

Further particular subgroups of the compounds of formula (I) are those compounds of formula (I), or any subgroup of compounds of formula (I) specified herein, wherein one of $R^{2a}$ and $R^{3a}$ is $C_{1-6}$alkyl and the other one of $R^{2a}$ and $R^{3a}$ is hydrogen; in case $R^{2a}$ is different from hydrogen then $R^{2b}$ is $C_{1-6}$alkyl, and $R^{3b}$ is hydrogen; in case $R^{3a}$ is different from hydrogen then $R^{3b}$ is $C_{1-6}$alkyl, and $R^{2b}$ is hydrogen.

Particular subgroups of compounds comprises the group of compounds or formula (I) or any subgroup specified herein, wherein $R^{2a}$, $R^{2b}$, $R^{3a}$ are hydrogen and $R^{3b}$ is $C_{1-6}$alkyl.

Other interesting compounds are those compounds of formula (I) including any subgroups of the compounds of formula (I) wherein t is 2.

Preferred compounds are those compounds listed in tables 1 through 3, more in particular the compound numbers 1 to 10 and 17 to 31.

The compounds of formula (I) or any of the subgroups thereof can be prepared as in the following reaction schemes.

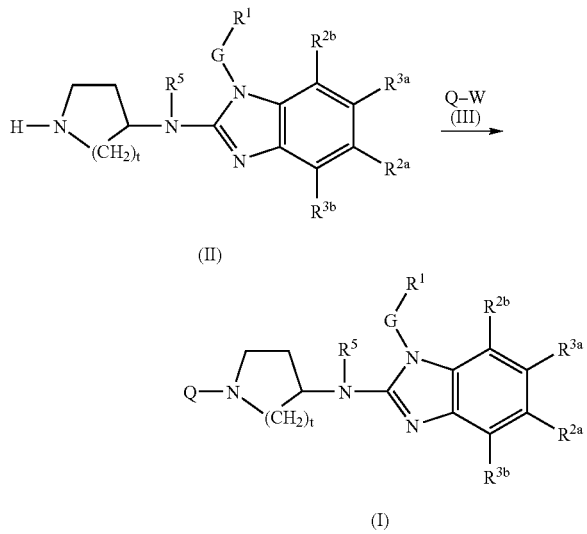

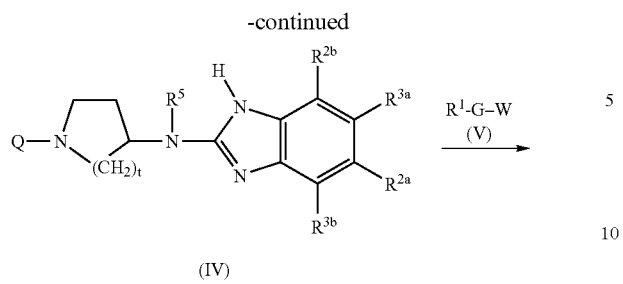

(IV)

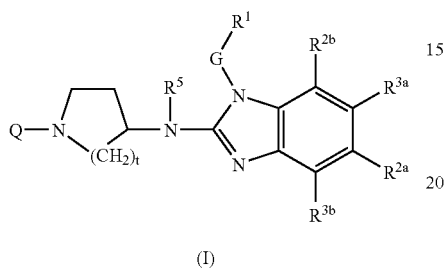

(I)

In these schemes Q, G, t, $R^1$, $R^{2a}$, $R^{2b}$, $R^{3a}$, $R^{3b}$, $R^5$ have the meanings defined above for the compounds of formula (I) or of any of the subgroups thereof. W is an appropriate leaving group, preferably it is chloro or bromo. The reactions of these schemes can be typically conducted in a suitable solvent such as an ether, e.g. THF, a halogenated hydrocarbon, e.g. dichloromethane, $CHCl_3$, toluene, a polar aprotic solvent such as DMF, DMSO, DMA and the like. A base may be added to pick up the acid that is liberated during the reaction. If desired, certain catalysts such as iodide salts (e.g. KI) may be added.

Compounds of formula (I) may be converted into each other following art-known functional group transformation reactions, comprising those described hereinafter. Compounds of formula (I) wherein $R^5$ is hydrogen may be converted to corresponding compounds of formula (I) wherein is other than hydrogen by an N-alkylation reaction which may be conducted under similar conditions as described above for the conversion of (II) or of (IV) to (I).

A number of the intermediates used to prepare the compounds of formula (I) are known compounds or are analogs of known compounds, which can be prepared following modifications of art-known methodologies readily accessible to the skilled person. A number of preparations of intermediates are given hereafter in somewhat more detail.

The intermediates of formula (II) and (IV) can be prepared as outlined in the following reaction schemes.

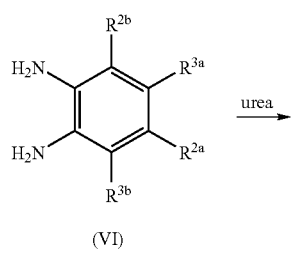

(VI)

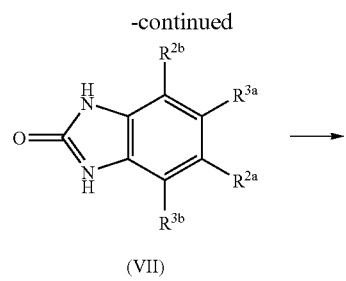

(VII)

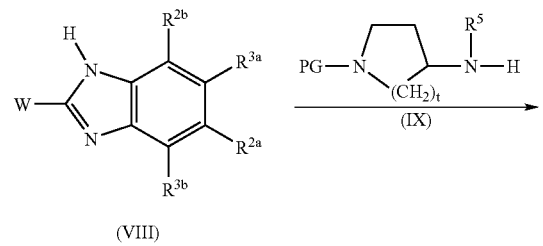

(VIII)

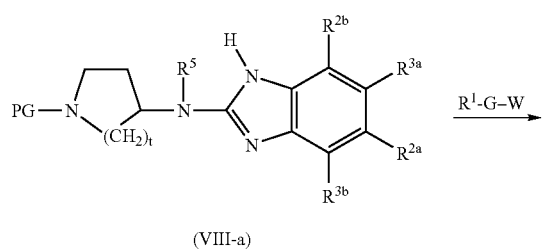

(VIII-a)

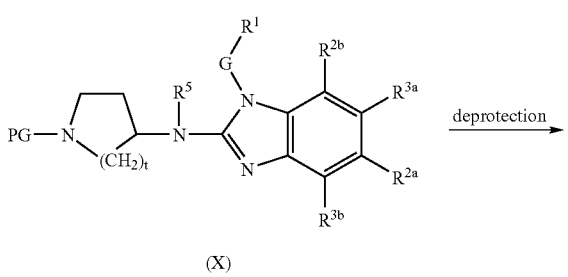

(X)

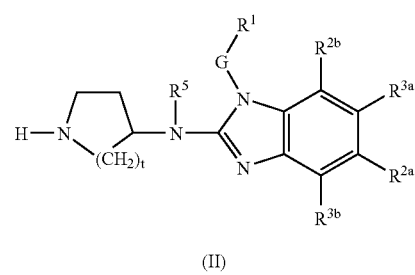

(II)

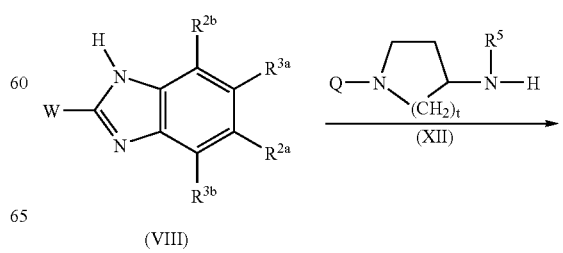

(VIII)

-continued

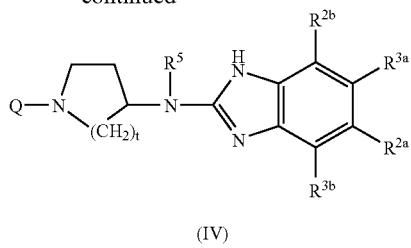

(IV)

In a first step, a diaminobenzene (VI) is cyclized with urea, preferably in a suitable solvent, e.g. xylene, to yield a benzimidazolone (VII). The latter is converted to a benzimidazole derivative (VIII) wherein W is a leaving group as specified above, in particular by reaction of (VII) with a suitable halogenating agent, for example $POCl_3$. The resulting intermediate (VIII) is reacted with the cyclic amine derivative (IX) in an N-alkylation reaction to obtain (VIII-a) which is converted with $R^1$-G-W to intermediate (X). The group PG in (IX) and (X) represents a suitable N-protecting group, e.g. an alkyloxycarbonyl group such as an ethyloxycarbonyl group, which can be readily removed, e.g. by a base to yield intermediates (II).

Intermediate (VIII) can be similarly reacted with a cyclic amine (XII) in an N-alkylation reaction to yield intermediate (IV). The above-mentioned N-alkylations are conducted in a suitable solvent and, if desired, in the presence of a base.

The compounds of formula (I) may be converted to the corresponding N-oxide forms following art-known procedures for converting a trivalent nitrogen into its N-oxide form. Said N-oxidation reaction may generally be carried out by reacting the starting material of formula (I) with an appropriate organic or inorganic peroxide. Appropriate inorganic peroxides comprise, for example, hydrogen peroxide, alkali metal or earth alkaline metal peroxides, e.g. sodium peroxide, potassium peroxide; appropriate organic peroxides may comprise peroxy acids such as, for example, benzenecarboperoxoic acid or halo substituted benzenecarboperoxoic acid, e.g. 3-chlorobenzenecarboperoxoic acid, peroxoalkanoic acids, e.g. peroxoacetic acid, alkylhydroperoxides, e.g. t.butyl hydro-peroxide. Suitable solvents are, for example, water, lower alcohols, e.g. ethanol and the like, hydrocarbons, e.g. toluene, ketones, e.g. 2-butanone, halogenated hydrocarbons, e.g. dichloromethane, and mixtures of such solvents.

Pure stereochemically isomeric forms of the compounds of formula (I) may be obtained by the application of art-known procedures. Diastereomers may be separated by physical methods such as selective crystallization and chromatographic techniques, e.g., counter-current distribution, liquid chromatography and the like.

The compounds of formula (I) as prepared in the hereinabove described processes are generally racemic mixtures of enantiomers which can be separated from one another following art-known resolution procedures. The racemic compounds of formula (I) which are sufficiently basic or acidic may be converted into the corresponding diastereomeric salt forms by reaction with a suitable chiral acid, respectively chiral base. Said diastereomeric salt forms are subsequently separated, for example, by selective or fractional crystallization and the enantiomers are liberated therefrom by alkali or acid. An alternative manner of separating the enantiomeric forms of the compounds of formula (I) involves liquid chromatography, in particular liquid chromatography using a chiral stationary phase. Said pure stereochemically isomeric forms may also be derived from the corresponding pure stereochemically isomeric forms of the appropriate starting materials, provided that the reaction occurs stereospecifically. Preferably if a specific stereoisomer is desired, said compound will be synthesized by stereospecific methods of preparation. These methods will advantageously employ enantiomerically pure starting materials.

In a further aspect, the present invention concerns a pharmaceutical composition comprising a therapeutically effective amount of a compound of formula (I) as specified herein, or a compound of any of the subgroups of compounds of formula (I) as specified herein, and a pharmaceutically acceptable carrier. A therapeutically effective amount in this context is an amount sufficient to prophylaxictically act against, to stabilize or to reduce viral infection, and in particular RSV viral infection, in infected subjects or subjects being at risk of being infected. In still a further aspect, this invention relates to a process of preparing a pharmaceutical composition as specified herein, which comprises intimately mixing a pharmaceutically acceptable carrier with a therapeutically effective amount of a compound of formula (I), as specified herein, or of a compound of any of the subgroups of compounds of formula (I) as specified herein.

Therefore, the compounds of the present invention or any subgroup thereof may be formulated into various pharmaceutical forms for administration purposes. As appropriate compositions there may be cited all compositions usually employed for systemically administering drugs. To prepare the pharmaceutical compositions of this invention, an effective amount of the particular compound, optionally in addition salt form or metal complex, as the active ingredient is combined in intimate admixture with a pharmaceutically acceptable carrier, which carrier may take a wide variety of forms depending on the form of preparation desired for administration. These pharmaceutical compositions are desirable in unitary dosage form suitable, particularly, for administration orally, rectally, percutaneously, or by parenteral injection. For example, in preparing the compositions in oral dosage form, any of the usual pharmaceutical media may be employed such as, for example, water, glycols, oils, alcohols and the like in the case of oral liquid preparations such as suspensions, syrups, elixirs, emulsions and solutions; or solid carriers such as starches, sugars, kaolin, lubricants, binders, disintegrating agents and the like in the case of powders, pills, capsules, and tablets. Because of their ease in administration, tablets and capsules represent the most advantageous oral dosage unit forms, in which case solid pharmaceutical carriers are obviously employed. For parenteral compositions, the carrier will usually comprise sterile water, at least in large part, though other ingredients, for example, to aid solubility, may be included. Injectable solutions, for example, may be prepared in which the carrier comprises saline solution, glucose solution or a mixture of saline and glucose solution. Injectable suspensions may also be prepared in which case appropriate liquid carriers, suspending agents and the like may be employed. Also included are solid form preparations which are intended to be converted, shortly before use, to liquid form preparations. In the compositions suitable for percutaneous administration, the carrier optionally comprises a penetration enhancing agent and/or a suitable wetting agent, optionally combined with suitable additives of any nature in minor proportions, which additives do not introduce a significant deleterious effect on the skin.

The compounds of the present invention may also be administered via oral inhalation or insufflation by means of methods and formulations employed in the art for administration via this way. Thus, in general the compounds of the present invention may be administered to the lungs in the form of a solution, a suspension or a dry powder, a solution being preferred. Any system developed for the delivery of solutions, suspensions or dry powders via oral inhalation or insufflation are suitable for the administration of the present compounds.

Thus, the present invention also provides a pharmaceutical composition adapted for administration by inhalation or insufflation through the mouth comprising a compound of formula (I) and a pharmaceutically acceptable carrier. Preferably, the compounds of the present invention are administered via inhalation of a solution in nebulized or aerosolized doses.

It is especially advantageous to formulate the aforementioned pharmaceutical compositions in unit dosage form for ease of administration and uniformity of dosage. Unit dosage form as used herein refers to physically discrete units suitable as unitary dosages, each unit containing a predetermined quantity of active ingredient calculated to produce the desired therapeutic effect in association with the required pharmaceutical carrier. Examples of such unit dosage forms are tablets (including scored or coated tablets), capsules, pills, suppositories, powder packets, wafers, injectable solutions or suspensions and the like, and segregated multiples thereof.

The compounds of formula (I) show antiviral properties. Viral infections treatable using the compounds and methods of the present invention include those infections brought on by ortho- and paramyxoviruses and in particular by human and bovine respiratory syncytial virus (RSV). A number of the compounds of this invention moreover are active against mutated strains of RSV. Additionally, many of the compounds of this invention show a favorable pharmacokinetic profile and have attractive properties in terms of bioavailability, including an acceptable half-life, AUC and peak values and lacking unfavourable phenomena such as insufficient quick onset and tissue retention.

The in vitro antiviral activity against RSV of the present compounds was tested in a test as described in the experimental part of the description, and may also be demonstrated in a virus yield reduction assay. The in vivo antiviral activity against RSV of the present compounds may be demonstrated in a test model using cotton rats as described in Wyde et al. (Antiviral Research (1998), 38, 31-42).

Due to their antiviral properties, particularly their anti-RSV properties, the compounds of formula (I) or any subgroup thereof, their prodrugs, N-oxides, addition salts, quaternary amines, metal complexes and stereochemically isomeric forms, are useful in the treatment of individuals experiencing a viral infection, particularly a RSV infection, and for the prophylaxis of these infections. In general, the compounds of the present invention may be useful in the treatment of warm-blooded animals infected with viruses, in particular the respiratory syncytial virus.

The compounds of the present invention or any subgroup thereof may therefore be used as medicines. Said use as a medicine or method of treatment comprises the systemic administration to viral infected subjects or to subjects susceptible to viral infections of an amount effective to combat the conditions associated with the viral infection, in particular the RSV infection.

The present invention also relates to the use of the present compounds or any subgroup thereof in the manufacture of a medicament for the treatment or the prevention of viral infections, particularly RSV infection.

The present invention furthermore relates to a method of treating a warm-blooded animal infected by a virus, or being at risk of infection by a virus, in particular by RSV, said method comprising the administration of an anti-virally effective amount of a compound of formula (I), as specified herein, or of a compound of any of the subgroups of compounds of formula (I), as specified herein.

In general it is contemplated that an antiviral effective daily amount would be from 0.01 mg/kg to 500 mg/kg body weight, more preferably from 0.1 mg/kg to 50 mg/kg body weight. It may be appropriate to administer the required dose as two, three, four or more sub-doses at appropriate intervals throughout the day. Said sub-doses may be formulated as unit dosage forms, for example, containing 1 to 1000 mg, and in particular 5 to 200 mg of active ingredient per unit dosage form.

The exact dosage and frequency of administration depends on the particular compound of formula (I) used, the particular condition being treated, the severity of the condition being treated, the age, weight, sex, extent of disorder and general physical condition of the particular patient as well as other medication the individual may be taking, as is well known to those skilled in the art. Furthermore, it is evident that said effective daily amount may be lowered or increased depending on the response of the treated subject and/or depending on the evaluation of the physician prescribing the compounds of the instant invention. The effective daily amount ranges mentioned hereinabove are therefore only guidelines.

Also, the combination of another antiviral agent and a compound of formula (I) can be used as a medicine. Thus, the present invention also relates to a product containing (a) a compound of formula (I), and (b) another antiviral compound, as a combined preparation for simultaneous, separate or sequential use in antiviral treatment. The different drugs may be combined in a single preparation together with pharmaceutically acceptable carriers. For instance, the compounds of the present invention may be combined with interferon-beta or tumor necrosis factor-alpha in order to treat or prevent RSV infections.

EXAMPLES

The following examples are intended to illustrate the present invention and not to limit it thereto. The terms "compound 1", "compound 4" etc used in these examples refer to the same compounds in the tables.

The compounds were analyzed by LC/MS using the following equipment:

LCT: electrospray ionisation in positive mode, scanning mode from 100 to 900 amu; Xterra MS C18 (Waters, Milford, Mass.) 5 µm, 3.9×150 mm); flow rate 1 ml/min. Two mobile phases (mobile phase A: 85% 6.5 mM ammonium acetate+15% acetonitrile; mobile phase B: 20% 6.5 mM ammonium acetate+80% acetonitrile) were employed to run a gradient from 100% A for 3 min to 100% B in 5 min., 100% B for 6 min to 100% A in 3 min, and equilibrate again with 100% A for 3 min).

ZQ: electrospray ionisation in both positive and negative (pulsed) mode scanning from 100 to 1000 amu; Xterra RP C18 (Waters, Milford, Mass.) 5 µm, 3.9×150 mm); flow rate 1 ml/min. Two mobile phases (mobile phase A: 85% 6.5 mM ammonium acetate+15% acetonitrile; mobile phase B: 20% 6.5 mM ammonium acetate+80% acetonitrile) were employed to run a gradient condition from 100% A for 3 min to 100% B in 5 min., 100% B for 6 min to 100% A in 3 min, and equilibrate again with 100% A for 3 min).

Example 1

Preparation of Dimethylbenzimidazole Intermediates

Scheme A-1

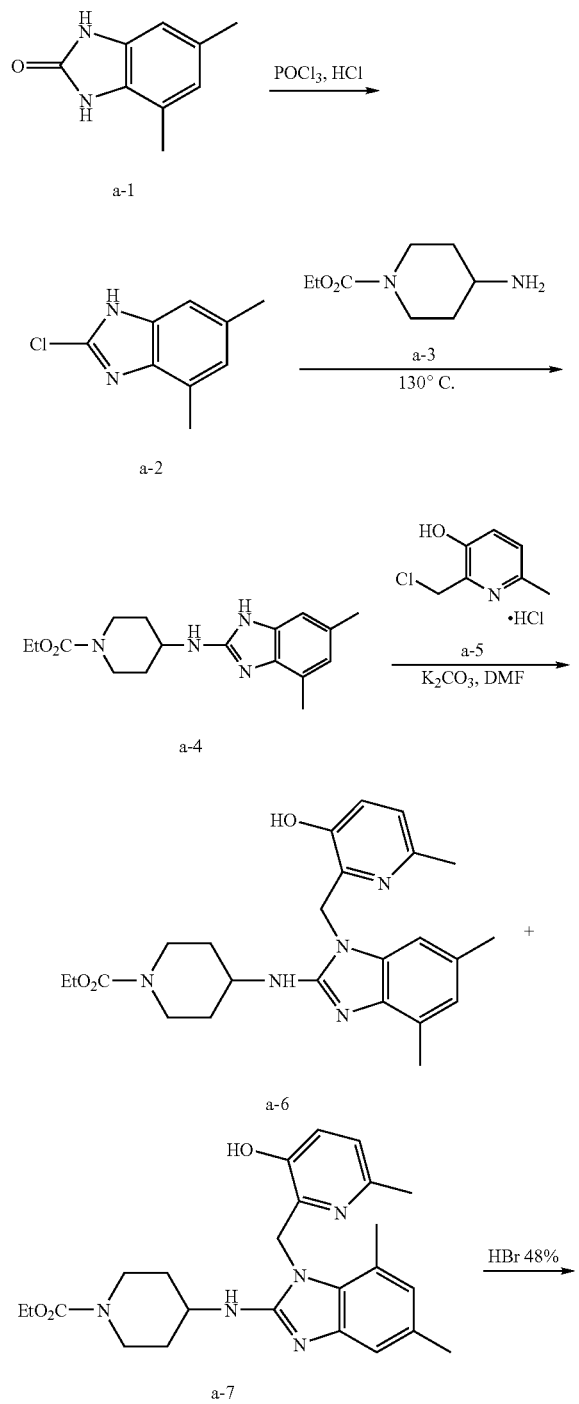

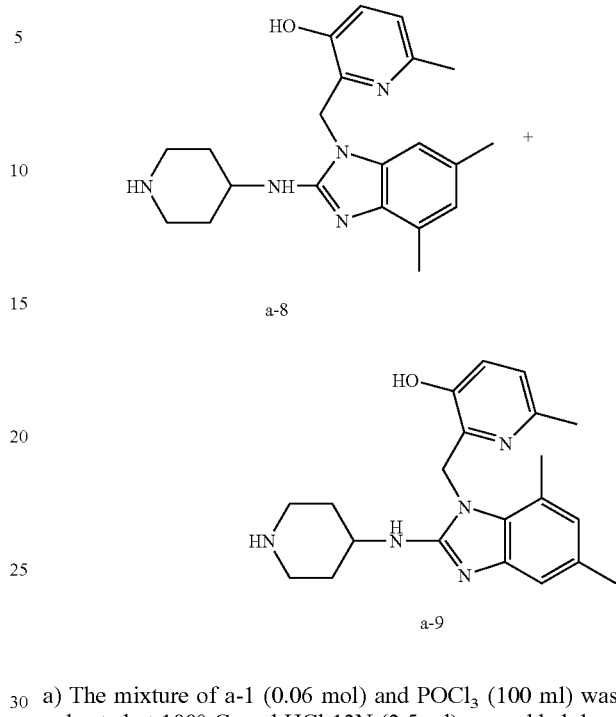

a) The mixture of a-1 (0.06 mol) and POCl₃ (100 ml) was heated at 100° C. and HCl 12N (2.5 ml) was added drop wise very carefully. The reaction was then stirred during 12 hours at 120° C. and allowed to cool down to room temperature. The solvent was evaporated under reduced pressure and a 10% solution of potassium carbonate in water was added to the residue. The resulting precipitate was filtered off, rinsed with water and dried, yielding 10 g of a-2 (93%, melting point=152° C.).

b) a-2 (0.022 mol) and a-3 (0.088 mol) were stirred at 130° C. during 12 hours. The reaction was then allowed to cool down to room temperature, the residue was taken up in acetone and the precipitate was filtered off. The acetone solution was concentrated under reduced pressure. The residue was purified by column chromatography over silica gel (eluent: CH₂Cl₂/MeOH/NH₄OH 95/5/0.1). The pure fractions were collected and the solvent was evaporated, yielding 5 g of a-4 (72%).

c) A mixture of a-4 (0.0158 mol), a-5 (0.019 mol) and potassium carbonate (0.0553 mol) in dimethylformamide (100 ml) was stirred at 70° C. for 24 hours. The solvent was evaporated until dryness. The residue was taken up in CH₂Cl₂/CH₃OH (90/10). The organic layer was washed with a 10% solution of K₂CO₃ in water, dried (over MgSO₄), filtered and the solvent was evaporated under reduced pressure. The residue was taken up in 2-propanone. The precipitate was filtered off, washed with H₂O and dried, yielding 5 g of a-6 and a-7 (50/50 mixture, 73%).

d) A mixture of a-6 and a-7 (0.0103 mol) in a 48% solution of HBr in water (50 ml) was stirred at 60° C. during 12 hours. The solvent was evaporated until dryness. The residue was taken up in CH₂Cl₂/CH₃OH (90/10). 10% solution of K₂CO₃ in water was added. The aqueous layer was saturated with K₂CO₃ (powder). The organic layer was separated, dried (over MgSO₄), filtered, and the solvent was evaporated until dryness, yielding 3.7 g of a-8 and a-9 (100%). This product was used directly in the next reaction step.

Example 2

Preparation of Dimethylbenzimidazole End Products

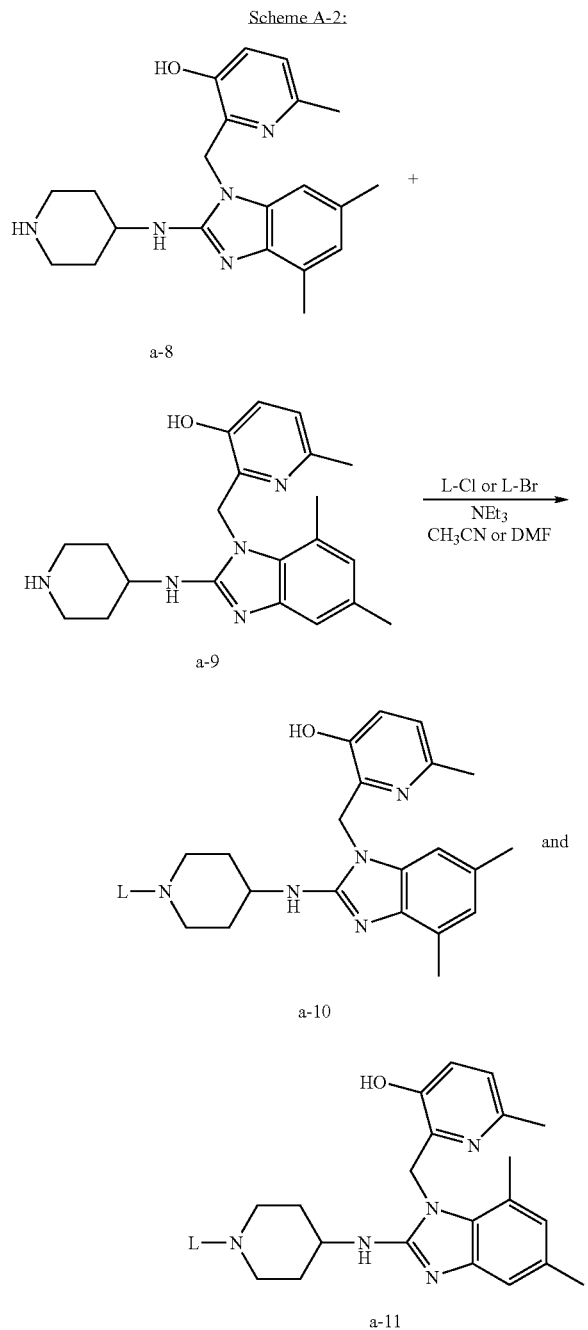

Variant 1:

A mixture of a-8 (0.0002 mol), a-9 (0.0002 mol), 2-bromo-ethanol (0.0006 mol) and triethylamine (0.0011 mol) in acetonitrile (10 ml) was stirred at 30° C. for 12 hours. The solvent was evaporated until dryness. The residue was taken up in $CH_2Cl_2$. The organic layer was washed with $H_2O$, dried (over $MgSO_4$), filtered, and the solvent was evaporated. The residue was purified by column chromatography over silica gel (eluent: $CH_2Cl_2/CH_3OH/NH_4OH$ 85/15/1; 10 μm). Two fractions were collected and the solvent was evaporated, yielding: 0.028 g fraction 1 (12.4%) and 0.05 g fraction 2 (22%). Fraction 1 was crystallized from 2-propanone/diisopropylether. The precipitate was filtered off and dried, yielding 0.015 g of 2-{2-[1-(2-hydroxy-ethyl)-piperidin-4-ylamino]-5,7-dimethyl-benzoimidazol-1-ylmethyl}-6-methyl-pyridin-3-ol (6.6%, melting point: 143° C.). Fraction 2 was crystallized from 2-propanone/diisopropylether. The precipitate was filtered off and dried, yielding 0.03 g of 2-{2-[1-(2-hydroxy-ethyl)-piperidin-4-ylamino]-4,6-dimethyl-benzoimidazol-1-ylmethyl}-6-methyl-pyridin-3-ol (compound 2, 13%, melting point: 177° C.).

Variant 2:

A mixture of a-8 (0.0008 mol), a-9 (0.0008 mol), 3-chloro-propane-sulfonamide (0.0019 mol) and triethylamine (0.0024 mol) in dimethylformamide (50 ml) was stirred at 70° C. for 12 hours, then poured out into $H_2O$ and extracted with $CH_2Cl_2$. The organic layer was separated, dried (over $MgSO_4$), filtered and the solvent was evaporated until dryness. The residue (1 g) was purified by column chromatography over silica gel (eluent: $CH_2Cl_2/CH_3OH/NH_4OH$ 90/10/0.5; 15-40 μm). The pure fractions were collected and the solvent was evaporated, yielding 0.12 g of 3-{4-[1-(3-hydroxy-6-methyl-pyridin-2-ylmethyl)-4,6-dimethyl-1H-benzoimidazol-2-ylamino]-piperidin-1-yl}-propane-1-sulfonic acid amide (compound 1, 15%, melting point: 180° C.).

Variant 3

$LiAlH_4$ (0.0002 mol) was added at 5° C. to a mixture of 3-{4-[1-(3-Hydroxy-6-methyl-pyridin-2-ylmethyl)-4,6-dimethyl-1H-benzoimidazol-2-ylamino]-piperidin-1-yl}-propionic acid ethyl ester (0.00009 mol; melting point: 172° C.; prepared according to the procedure described in variant 2) in tetrahydrofuran (10 ml) under $N_2$ flow. The mixture was stirred at 5° C. for 1 hour, then at room temperature for 3 hours. A minimum of $H_2O$ and ethylacetate were added. The organic layer was separated, dried (over $MgSO_4$), filtered and the solvent was evaporated until dryness. The residue was crystallized from 2-propanone/$CH_3CN$/diisopropylether. The precipitate was filtered off and dried, yielding 0.026 g of 2-{2-[1-(3-hydroxy-propyl)-piperidin-4-ylamino]-4,6-dimethyl-benzoimidazol-1-ylmethyl}-6-methyl-pyridin-3-ol (compound 4, 68%, melting point: 209° C.).

Variant 4

A mixture of 3-{4-[1-(3-Hydroxy-6-methyl-pyridin-2-ylmethyl)-4,6-dimethyl-1H-benzoimidazol-2-ylamino]-piperidin-1-yl}-propionic acid ethyl ester (0.0065 mol) in methanol/$NH_3$ 7N (15 ml) was stirred in a sealed vessel at 70° C. for 12 hours. The solvent was evaporated until dryness. The residue (0.3 g) was purified by column chromatography over silica gel (eluent: $CH_2Cl_2/CH_3OH/NH_4OH$ 85/14/1; 5 μm). The pure fractions were collected and the solvent was evaporated. The residue (0.09 g, 32%) was crystallized from diisopropylether. The precipitate was filtered off and dried, yielding 0.086 g of 3-{4-[1-(3-hydroxy-6-methyl-pyridin-2-ylmethyl)-4,6-dimethyl-1H-benzoimidazol-2-ylamino]-piperidin-1-yl}-propionamide (compound 5, 30%, melting point: 212° C.).

TABLE 1
compounds prepared according to scheme A-2
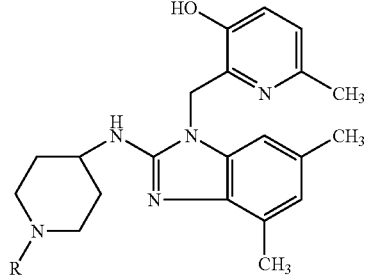
| Comp. No. | —R | Activity | Mass Spectroscopy | Melting point | variant |
|---|---|---|---|---|---|
| 1 | 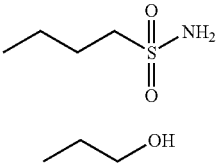 | 8.7 | MH$^+$ = 487 | 180° C. | 2 |
| 2 | 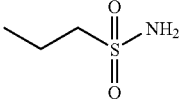 | 8.5 | MH$^+$ = 410 | 177° C. | 1 |
| 3 |  | 8.5 | MH$^+$ = 473 | 242° C. | 2 |
| 4 | 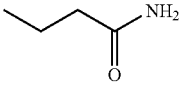 | 8.1 | MH$^+$ = 424 | 209° C. | 3 |
| 5 | 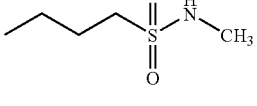 | | MH$^+$ = 437 | 212° C. | 4 |
| 6 | 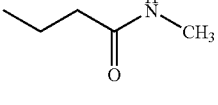 | 7.8 | MH$^+$ = 501 | 179° C. | 2 |
| 7 |  | 7.6 | MH$^+$ = 451 | 186° C. | 4 |
| 8 | 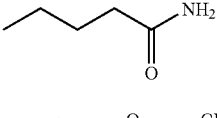 | 7.6 | MH$^+$ = 438 | 206° C. | 3 |
| 9 | 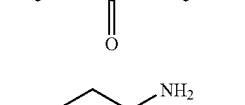 | 7.4 | MH$^+$ = 451 | 206° C. | 4 |
| 10 | 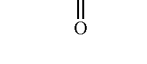 | 7.1 | MH$^+$ = 466 | 172° C. | 2 |
| 11 | 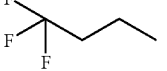 | 6.8 | MH$^+$ = 423 | 226° C. | 4 |
| 12 |  | 6.8 | MH$^+$ = 462 | >260° C. | 2 |

TABLE 1-continued
compounds prepared according to scheme A-2
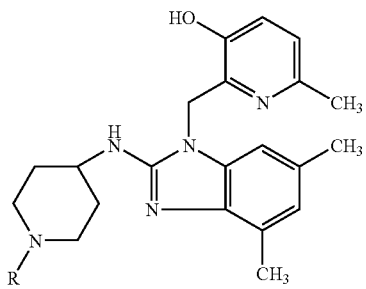
| Comp. No. | —R | Activity | Mass Spectroscopy | Melting point | variant |
|---|---|---|---|---|---|
| 13 | -O-CH2-CH3) | 6.5 | MH+ = 452 | 186° C. | 1 |
| 14 | | 6.5 | MH+ = 471 | 161° C. | 2 |
TABLE 2
Further compounds prepared according to scheme A-2
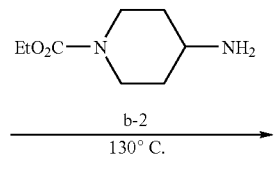
| Comp. No. | R | Activity | Mass Spectroscopy | Melting point | variant |
|---|---|---|---|---|---|
| 15 | | 6.4 | MH+ = 410 | 143° C. | 1 |
| 16 | -O-CH2-CH3) | 5.8 | MH+ = 452 | 186° C. | 2 |
Example 3
Preparation of Methylbenzimidazole Intermediates
Scheme B-1
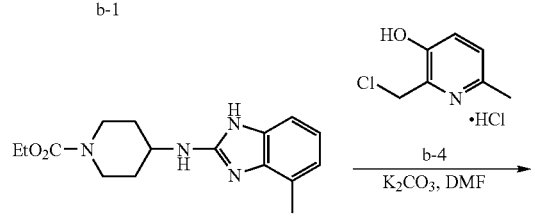
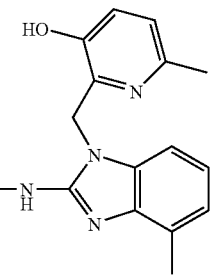

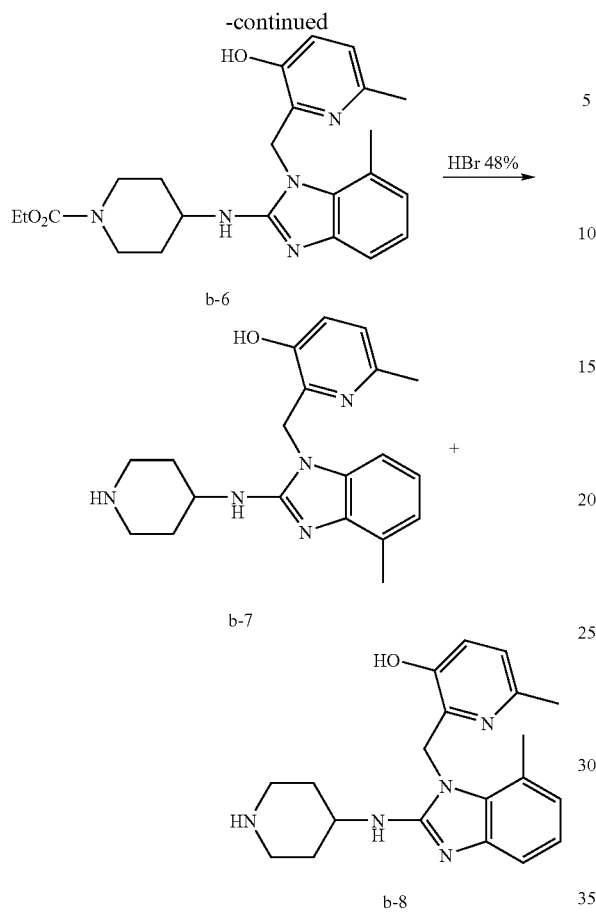

a) The preparation of this intermediate b-3 is analogous to the preparation of intermediate a-4.
b) The preparation of these intermediates b-5 and b-6 is analogous to the preparation of intermediates a-6 and a-7.
c) The preparation of these intermediates b-7 and b-8 is analogous to the preparation of intermediates a-8 and a-8. Further to that, b-7 has been isolated pure after crystallization with diisopropylether (melting point: >260° C.).

Example 4

Preparation of Methylbenzimidazole Intermediates End Products

Scheme B-2

Variant 1

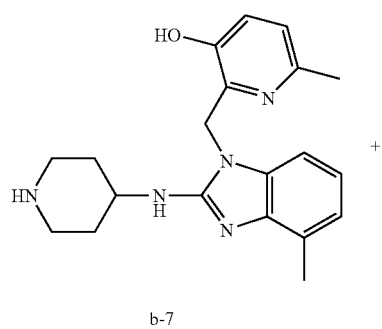

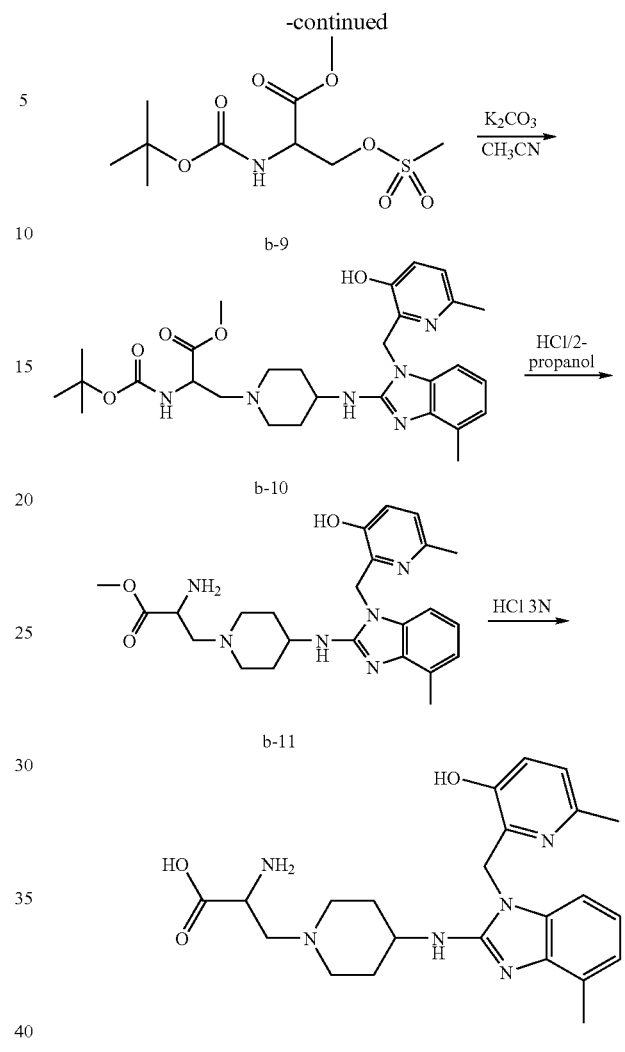

a) A mixture of b-7 (0.0056 mol), b-9 (0.0113 mol) and $K_2CO_3$ (0.0171 mol) in $CH_3CN$ (30 ml) was stirred and refluxed for 6 hours. The solvent was evaporated. The residue was taken up in $CH_2Cl_2$ and washed with a saturated solution of NaCl in water. The organic layer was separated, dried (over $MgSO_4$), filtered and the solvent was evaporated. The residue (2.4 g) was purified by column chromatography over silica gel (eluent: $CH_2Cl_2$/$CH_3OH$/$NH_4OH$ 95/5/0.2; 15-40 µm). The pure fractions were collected and the solvent was evaporated, yielding 1 g of intermediate b-10 (32%).

b) A saturated solution of HCl in 2-propanol (1.5 ml) was added at room temperature to a mixture of b-10 (0.0013 mol) in 2-propanol (15 ml). The mixture was stirred at 60° C. for 12 hours, and then cooled to room temperature. The precipitate was filtered, washed with 2-propanol, then with diethyl ether and dried, yielding 0.79 g. This fraction was crystallized from 2-propanol. The precipitate was filtered, washed with diethyl ether and dried, yielding 0.11 g of b-11 (14%).

c) A mixture of b-11 (0.0011 mol) in a 3N solution of HCl in water (5 ml) was stirred and refluxed for 6 hours, then cooled to room temperature and the solvent was evaporated. The residue (0.4 g) was purified by column chromatography over silica gel (eluent: CH₂Cl₂/CH₃OH/NH₄OH 70/30/3; 15-40 µm). Two fractions were collected and the solvent was evaporated. Yielding: 0.111 g. This fraction was crystallized from ethanol. The precipitate was filtered off and dried, yielding 0.03 g of b-12 (compound 23, 5%, melting point: 195° C.).

Variant 2:

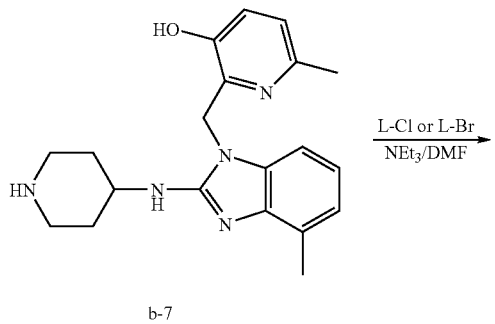

b-7

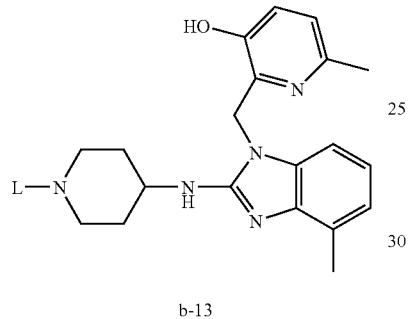

b-13

3-{4-[1-(3-hydroxy-6-methyl-pyridin-2-ylmethyl)-4-methyl-1H-benzoimidazol-2-ylamino]-piperidin-1-yl}-propane-1-sulfonic acid amide (compound 19, melting point: 250° C.) was prepared analogous to the procedure described in variant 2, scheme A-2.

Variant 3:

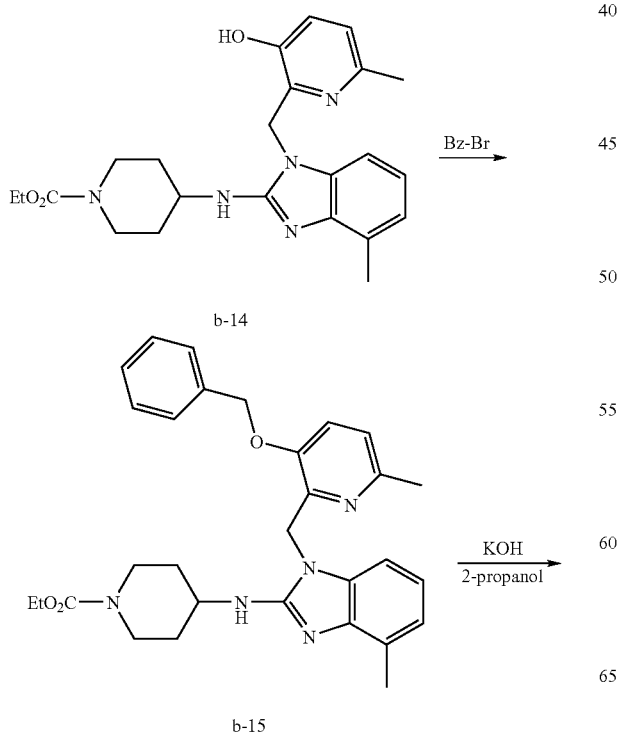

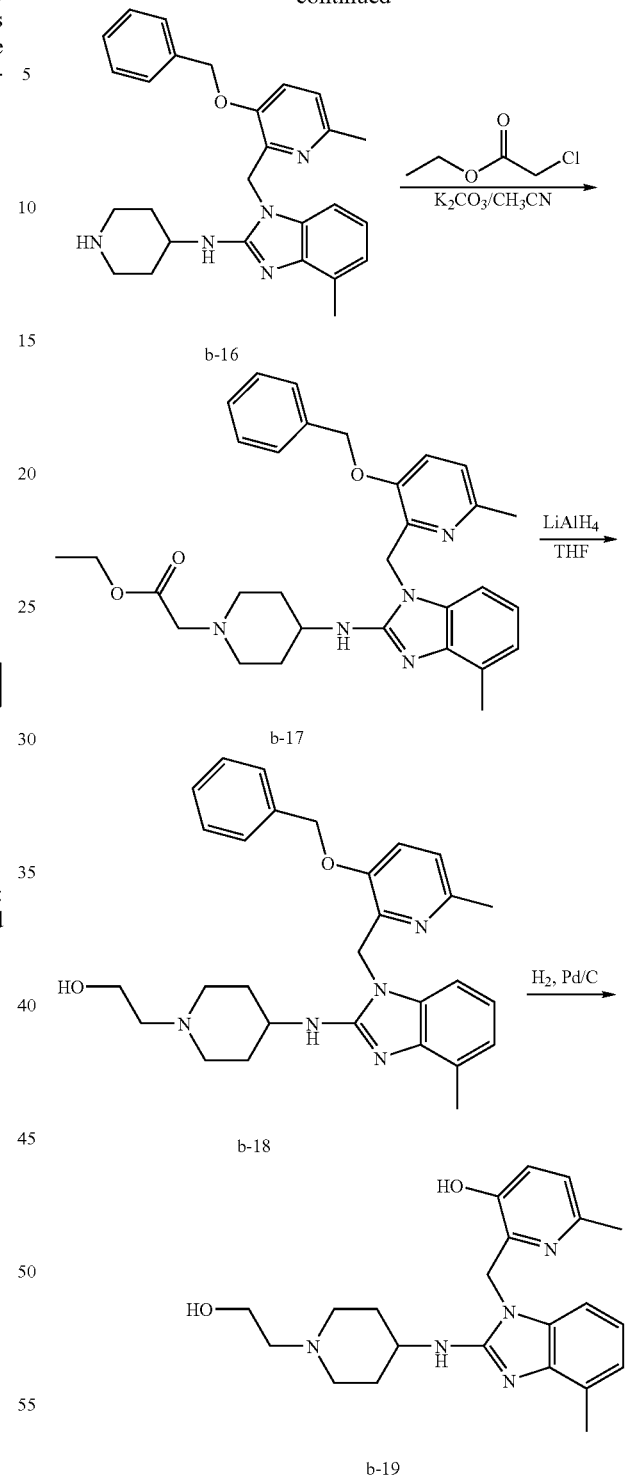

a) A mixture of b-14 (0.0236 mol), benzyl bromide (Bz-Br, 0.026 mol) and K₂CO₃ (0.0354 mol) in a mixture of CH₃CN (50 ml), dimethylformamide (50 ml) and tetrahydrofuran (100 ml) was stirred at 60° C. for 24 hours. The solvent was evaporated until dryness. The residue was taken up in H₂O. The precipitate was filtered, washed with H₂O and extracted with diethyl ether. The organic layer was separated, dried (over MgSO₄), filtered and the solvent was evaporated until dryness. The residue (12 g) was purified by column chromatography over silica gel (eluent: CH$_2$Cl$_2$/CH$_3$OH/NH$_4$OH 98/2/0.1; 15-40 μm). Three fractions were collected and the solvent was evaporated, yielding 5 g of b-15 (41.3%).

b) A mixture of b-15 (0.0095 mol) and KOH (0.0095 mol) in 2-propanol (60 ml) was stirred and refluxed for 4 hours. The solvent was evaporated until dryness. The residue was taken up in CH$_2$Cl$_2$. The organic layer was washed with H$_2$O, dried (over MgSO$_4$), filtered and the solvent was evaporated until dryness, yielding 5 g of b-16 (>100%, melting point: 182° C.). The product was used directly in the next reaction step.

c) A mixture of b-16 (0.0307 mol), ethyl chloro-acetate (0.037 mol) and K$_2$CO$_3$ (0.046 mol) in CH$_3$CN (150 ml) was stirred at 60° C. for 12 hours. The solvent was evaporated until dryness. The residue was taken up in CH$_2$Cl$_2$. The organic layer was washed with H$_2$O, dried (over MgSO$_4$), filtered and the solvent was evaporated until dryness. The residue was crystallized from 2-propanone/CH$_3$CN. The precipitate was filtered off and dried, yielding 14.5 g of b-17 (89.5%, melting point: 116° C.).

d) LiAlH$_4$ (0.047 mol) was added portion wise at 5° C. to a mixture of b-17 (0.023 mol) in tetrahydrofuran (250 ml) under N$_2$ flow. The mixture was stirred at 5° C. for 2 hours. H$_2$O was added. The mixture was extracted with ethylacetate and filtered over celite. The organic layer was separated, dried (over MgSO$_4$), filtered and the solvent was evaporated until dryness, yielding 8 g of b-18 (71.6%, melting point: 159° C.).

e) A mixture of b-18 (0.0004 mol) and Pd/C (0.1 g) in CH$_3$OH (20 ml) was hydrogenated at 40° C. for 3 hours under a 5 bar pressure, then cooled and filtered over celite. The filtrate was evaporated until dryness, yielding 0.16 g (100%). This fraction was crystallized from 2-propanone/diisopropylether. The precipitate was filtered off and dried, yielding 0.07 g of b-19 (compound 22, 43%, melting point: 258° C.).

Variant 4:

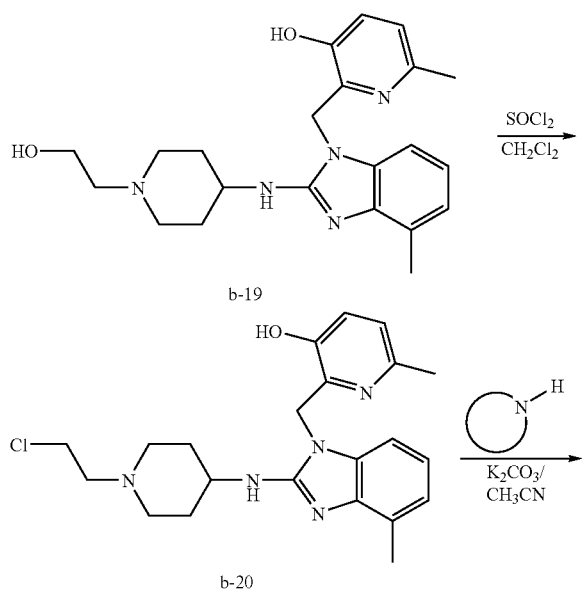

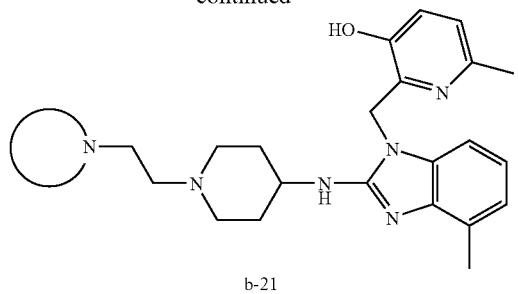

a) SOCl$_2$ (0.0214 mol) was added drop wise to a solution of b-19 in CH$_2$Cl$_2$ at 0° C. The reaction was stirred at room temperature for 5 hours. The precipitate was filtered off, rinsed with diisopropylether and dried, yielding b-20 (100%). The crude compound was used in the next reaction step.

b) A mixture of b-20 (0.0011 mol), K$_2$CO$_3$ (0.0038 mol) and pyrrolidine (0.0013 mol) in CH$_3$CN (10 ml) was stirred at 70° C. for 12 hours. H$_2$O was added. The mixture was extracted with CH$_2$Cl$_2$. The organic layer was separated, dried (over MgSO$_4$), filtered and the solvent was evaporated. The residue (0.27 g) was purified by column chromatography over silica gel (eluent: CH$_2$Cl$_2$/CH$_3$OH/NH$_4$OH 88/11/1; 10 μm). The pure fractions were collected and the solvent was evaporated. The residue (0.14 g) was crystallized from CH$_3$CN/2-propanone. The precipitate was filtered off and dried, yielding 0.105 g of 6-Methyl-2-{4-methyl-2-[1-(2-pyrrolidin-1-yl-ethyl)-piperidin-4-ylamino]-benzoimidazol-1-ylmethyl}-pyridin-3-ol (compound 18, 28%, melting point: 225° C.).

Variant 5 a) 3-{4-[1-(3-Hydroxy-6-methyl-pyridin-2-ylmethyl)-4-methyl-1H-benzoimidazol-2-ylamino]-piperidin-1-yl}-propionic acid ethyl ester (melting point: 226° C.) was prepared analogous to the procedure described for the preparation of b-19.

b) 3-{4-[1-(3-Hydroxy-6-methyl-pyridin-2-ylmethyl)-4-methyl-1H-benzoimidazol-2-ylamino]-piperidin-1-yl}-propionamide (compound 27, melting point: 258° C.) was prepared according to the procedure described in variant 4, scheme A-2.

Variant 6 a) A mixture of b-18 (0.002 mol), phenyl-acetic acid (0.0024 mol), DCC (0.0029 mol) and DMAP (0.0029 mol) in THF (50 ml) was stirred at room temperature for 12 hours. H$_2$O was added. The mixture was extracted with ethylacetate and filtered. The organic layer was separated, dried (over MgSO$_4$), filtered and the solvent was evaporated until dryness. The residue (1.5 g) was purified by column chromatography over silica gel (eluent: CH$_2$Cl$_2$/CH$_3$OH/NH$_4$OH 96/4/0.1; 15-35 μm). The pure fractions were collected and the solvent was evaporated. The residue (1.2 g, 96%) was crystallized from diisopropylether. The precipitate was filtered off and dried, yielding 0.8 g of phenylacetic acid-2-{4-[1-(3-benzyloxy-6-methyl-pyridin-2-ylmethyl)-4-methyl-1H-benzoimidazol-2-ylamino]-piperidin-1-yl}-ethyl ester (64%, melting point: 105° C.).

b) Phenyl-acetic acid 2-{4-[1-(3-hydroxy-6-methyl-pyridin-2-ylmethyl)-4-methyl-1H-benzoimidazol-2-ylamino]-piperidin-1-yl}-ethyl ester (compound 24, melting point: 207° C.) was prepared analogous to the procedure described for b-19.

Variant 7:
a) A mixture of 3-{4-[1-(3-Hydroxy-6-methyl-pyridin-2-ylmethyl)-4-methyl-1H-benzoimidazol-2-ylamino]-piperidin-1-yl}-propionic acid ethyl ester (0.0009 mol) in a 3N solution of HCl in water (5 ml) was stirred and refluxed for 18 hours and then cooled to room temperature. The precipitate was filtered, washed with diethyl ether and dried, yielding 0.18 g of 3-{4-[1-(3-hydroxy-6-methyl-pyridin-2-ylmethyl)-4-methyl-1H-benzoimidazol-2-ylamino]-piperidin-1-yl}-propionic acid hydrochloride salt (compound 33, 31%, melting point: 245° C.).

Variant 8:
a) 1-{4-[1-(3-Hydroxy-6-methyl-pyridin-2-ylmethyl)-4-methyl-1H-benzoimidazol-2-ylamino]-piperidin-1-yl}-3-methyl-butan-2-one was prepared analogous to the procedure described for b-19.
b) NaBH$_4$ (0.0003 mol) was added portion wise to a solution of 1-{4-[1-(3-Hydroxy-6-methyl-pyridin-2-ylmethyl)-4-methyl-1H-benzoimidazol-2-ylamino]-piperidin-1-yl}-3-methyl-butan-2-one (0.0002 mol) in tetrahydrofuran (2 ml) and CH$_3$OH (2 ml) at 5° C. The mixture was stirred at room temperature for 4 hours. 10% solution of K$_2$CO$_3$ in water was added. The mixture was extracted with CH$_2$Cl$_2$. The organic layer was washed with H$_2$O, dried (over MgSO$_4$), filtered and the solvent was evaporated. The residue (0.08 g) was dissolved in CH$_2$Cl$_2$/CH$_3$OH and crystallized from diisopropylether. The precipitate was filtered, washed with diisopropylether and dried, yielding 0.049 g of 2-{2-[1-(2-hydroxy-3-methyl-butyl)-piperidin-4-ylamino]-4-methyl-benzoimidazol-1-ylmethyl}-6-methyl-pyridin-3-ol (compound 35, 48%, melting point: 230° C.).

Variant 9:
a) Chlorosulfonyl isocyanate (0.0021 mol) was added at −30° C. to a mixture of b-18 (0.0009 mol) in ethylacetate (15 ml) under N$_2$ flow. The mixture was stirred at −30° C. for 1 hour, then brought to 0° C. H$_2$O (0.5 ml), HCl 12N (0.5 ml) then CH$_3$OH (1 ml) was added. The mixture was stirred at 40° C. for 1 hour, then cooled, basified with K$_2$CO$_3$ and extracted with ethylacetate. The organic layer was separated, dried (over MgSO$_4$), filtered and the solvent was evaporated until dryness, yielding 0.46 g of carbamic acid 2-{4-[1-(3-benzyloxy-6-methyl-pyridin-2-ylmethyl)-4-methyl-1H-benzoimidazol-2-ylamino]-piperidin-1-yl}-ethyl ester (94%).
b) Carbamic acid 2-{4-[1-(3-hydroxy-6-methyl-pyridin-2-ylmethyl)-4-methyl-1H-benzoimidazol-2-ylamino]-piperidin-1-yl}-ethyl ester (compound 37, melting point: 222° C.) has been prepared analogous to the procedure described for b-19.

Variant 10:
A mixture of b-7 (0.0014 mol), glycidyl 4-methoxyphenyl ether (0.0021 mol) in ethanol (10 ml) was stirred and refluxed for 4 hours, then cooled to room temperature and the solvent was evaporated. The residue (0.75 g) was purified by column chromatography over silica gel (eluent: CH$_2$Cl$_2$/CH$_3$OH 90/10; 15-40 µm). The pure fractions were collected and the solvent was evaporated, yielding 0.101 g of 2-(2-{1-[2-hydroxy-3-(4-methoxy-phenoxy)-propyl]-piperidin-4-ylamino}-4-methyl-benzoimidazol-1-ylmethyl)-6-methyl-pyridin-3-ol (compound 41, 13%, melting point: 227° C.).

Variant 11:
Formaldehyde 37% in water (0.0017 mol) and NaBH$_3$CN (0.001 mol) were added at room temperature to a mixture of b-7 (0.0008 mol) in CH$_3$CN (1 ml). Acetic acid (0.3 ml) was added drop wise. The mixture was stirred at room temperature overnight. The solvent was evaporated until dryness. Ethanol (3 ml) and a saturated solution of HCl in 2-propanol (1 ml) were added. The mixture was stirred at 80° C. for 2 hours, basified with K$_2$CO$_3$ 10% in water and extracted with CH$_2$Cl$_2$. The organic layer was separated, dried (over MgSO$_4$), filtered and the solvent was evaporated. The residue (0.21 g) was purified by column chromatography over silica gel (eluent: CH$_2$Cl$_2$/CH$_3$OH/NH$_4$OH 90/10/0.1 to 80/20/3; 35-70 µm). The pure fractions were collected and the solvent was evaporated until dryness, yielding 0.1 g of 6-methyl-2-[4-methyl-2-(1-methyl-piperidin-4-ylamino)-benzoimidazol-1-ylmethyl]-pyridin-3-ol, Compound 34 (32%, melting point: 210° C.).

TABLE 3 compounds prepared according to Scheme B-2

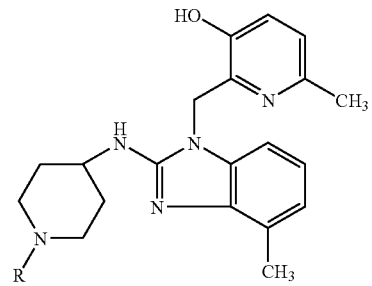

| Comp. No. | R | Activity | Mass Spectroscopy | Melting point | Variant | Salt |
|---|---|---|---|---|---|---|
| 17 | NH$_2$ group with ester | 8.7 | MH+ = 452 | 210° C. | 1 | HCl |

TABLE 3-continued
compounds prepared according to Scheme B-2
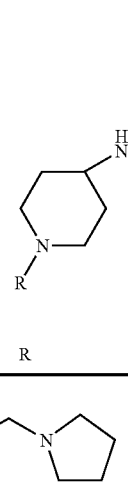
| Comp. No. | R | Activity | Mass Spectroscopy | Melting point | Variant | Salt |
|---|---|---|---|---|---|---|
| 18 | 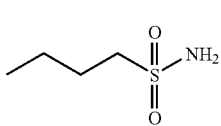 | 8.0 | MH+ = 449 | 225° C. | 4 | |
| 19 | 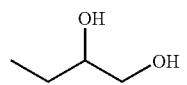 | 7.9 | MH+ = 473 | 250° C. | 2 | |
| 20 | 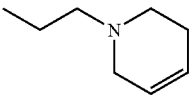 | 7.9 | MH+ = 426 | 240° C. | 2 | |
| 21 | 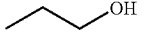 | 7.8 | MH+ = 461 | — | 4 | |
| 22 | 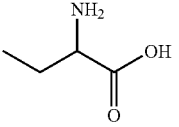 | 7.7 | MH+ = 396 | 258° C. | 3 | |
| 23 | 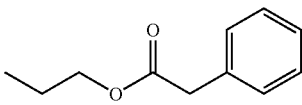 | 7.6 | MH+ = 437 | 195° C. | 1 | HCl |
| 24 | 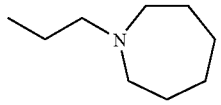 | 7.5 | MH+ = 514 | 207° C. | 6 | |
| 25 | 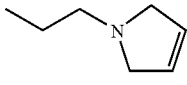 | 7.5 | MH+ = 477 | | 4 | |
| 26 | 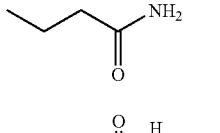 | 7.4 | MH+ = 447 | | 4 | |
| 27 |  | 7.3 | MH+ = 423 | 258° C. | 5 | |
| 28 |  | 7.3 | MH+ = 487 | 217° C. | 2 | |

TABLE 3-continued compounds prepared according to Scheme B-2

| Comp. No. | R | Activity | Mass Spectroscopy | Melting point | Variant | Salt |
|---|---|---|---|---|---|---|
| 29 | (2-methylpropan-1-ol, with CH3) | 7.2 | MH+ = 424 | >260° C. | 3 | |
| 30 | (propanoic acid) | 5.2 | MH+ = 410 | 205° C. | 7 | HCl |
| 31 | (hexanamide) | 7.1 | MH+ = 451 | 220° C. | 2 | |
| 32 | (ethyl butanoate) | 6.8 | MH+ = 452 | 226° C. | 2 | |
| 33 | (butanoic acid) | 6.8 | MH+ = 424 | 245° C. | 7 | HCl |
| 34 | —CH3 | 6.8 | MH+ = 466 | 210° C. | 11 | |
| 35 | (2-methylpentan-3-ol) | 6.8 | MH+ = 438 | 230° C. | 8 | |
| 36 | (4-butoxybenzenesulfonamide) | 6.8 | MH+ = 565 | >260° C. | 2 | |
| 37 | (propyl carbamate) | 6.8 | MH+ = 439 | 222° C. | 9 | |
| 38 | (propylimidazole) | 6.8 | MH+ = 446 | | 4 | |
| 39 | (1-phenylpropan-1-ol) | 6.6 | MH+ = 472 | 229° C. | 8 | |

TABLE 3-continued
compounds prepared according to Scheme B-2
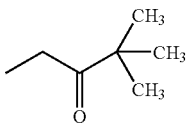
| Comp. No. | R | Activity | Mass Spectroscopy | Melting point | Variant | Salt |
|---|---|---|---|---|---|---|
| 40 | 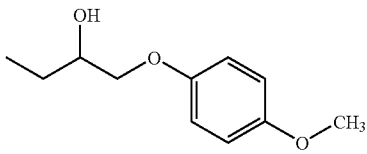 | 6.5 | MH+ = 450 | 230° C. | 3 | |
| 41 | 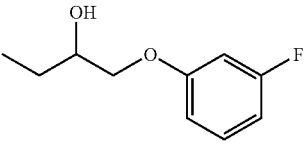 | 6.5 | MH+ = 532 | 227° C. | 10 | |
| 42 | 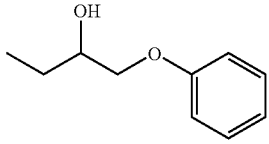 | 6.5 | MH+ = 520 | 230° C. | 10 | |
| 43 | 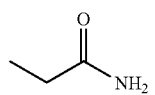 | 6.5 | MH+ = 502 | 228° C. | 10 | |
| 44 | 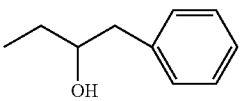 | 6.4 | MH+ = 409 | 254° C. | 5 | |
| 45 | 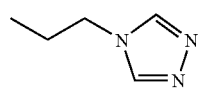 | 6.4 | MH+ = 486 | 158° C. | 10 | |
| 46 | 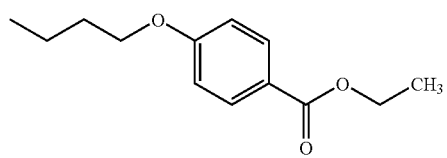 | 6.4 | MH+ = 447 | | 4 | |
| 47 | 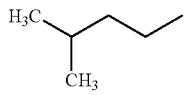 | 6.3 | MH+ = 558 | 228° C. | 2 | |
| 48 |  | 6.2 | MH+ = 422 | 230° C. | 3 | |

TABLE 3-continued compounds prepared according to Scheme B-2

| Comp. No. | R | Activity | Mass Spectroscopy | Melting point | Variant | Salt |
|---|---|---|---|---|---|---|
| 49 | (2-methyl-3-oxopentan-2-yl type: H3C-CH(CH3)-C(=O)-CH2CH3) | 6.1 | MH+ = 436 | | 3 | |
| 50 | (2-methyl-3-hydroxy: (CH3)2C(OH)-CH(CH3)-... / 2-hydroxy-2-methylbutyl) | 6.1 | MH+ = 452 | 255° C. | 8 | |
| 51 | (propoxyacetic acid methyl ester substituent) | 5.9 | MH+ = 468 | 105° C. | 6 | |
| 52 | (3-butoxybenzoic acid ethyl ester substituent) | 5.8 | MH+ = 558 | 196° C. | 2 | |
| 53 | (ethoxycarbonylmethoxy-ethyl substituent) | 5.7 | MH+ = 438 | 159° C. | 3 | |
| 54 | (1-ethyl-1-hydroxycyclohexyl) | 5.7 | MH+ = 464 | >260° C. | 10 | |

Example 5

In Vitro Screening for Activity Against Respiratory Syncytial Virus

The percent protection against cytopathology caused by viruses (antiviral activity or $EC_{50}$) achieved by tested compounds and their cytotoxicity ($CC_{50}$) are both calculated from dose-response curves. The selectivity of the antiviral effect is represented by the selectivity index (SI), calculated by dividing the $CC_{50}$ (cytotoxic dose for 50% of the cells) by the $EC_{50}$ (antiviral activity for 50% of the cells). The tables in the above experimental part list the category to which each of the prepared compounds belong: Compounds belonging to activity category "A" have an $pEC_{50}$ (−log of $EC_{50}$ when expressed in molar units) equal to or more than 7. Compounds belonging to activity category "B" have a pEC50 value between 6 and 7. Compounds belonging to activity category "C" have a pEC50 value equal to or below 6.

Automated tetrazolium-based calorimetric assays were used for determination of $EC_{50}$ and $CC_{50}$ of test compounds. Flat-bottom, 96-well plastic microtiter trays were filled with 180 μl of Eagle's Basal Medium, supplemented with 5% FCS (0% for FLU) and 20 mM Hepes buffer. Subsequently, stock solutions (7.8× final test concentration) of compounds were added in 45 μl volumes to a series of triplicate wells so as to allow simultaneous evaluation of their effects on virus- and mock-infected cells. Five five-fold dilutions were made directly in the microtiter trays using a robot system. Untreated virus controls, and HeLa cell controls were included in each test. Approximately 100 $TCID_{50}$ of Respiratory Syncytial Virus was added to two of the three rows in a volume of 50 μl. The same volume of medium was added to the third row to measure the cytotoxicity of the compounds at the same concentrations as those used to measure the antiviral activity. After two hours of incubation, a suspension (4×10$^5$ cells/ml) of HeLa cells was added to all wells in a volume of 50 μl. The cultures were incubated at 37° C. in a 5% CO$_2$ atmosphere. Seven days after infection the cytotoxicity and the antiviral activity was examined spectrophotometrically. To each well of the microtiter tray, 25 μl of a solution of MTT (3-(4,5-dimethylthiazol-2-yl)-2,5-diphenyltetrazolium bromide) was added. The trays were further incubated at 37° C. for 2 hours, after which the medium was removed from each cup. Solubilization of the formazan crystals was achieved by adding 100 μl 2-propanol. Complete dissolution of the formazan crystals were obtained after the trays have been placed on a plate shaker for 10 min. Finally, the absorbances were read in an eight-channel computer-controlled photometer (Multiskan MCC, Flow Laboratories) at two wavelengths (540 and 690 nm). The absorbance measured at 690 nm was automatically subtracted from the absorbance at 540 nm, so as to eliminate the effects of non-specific absorption.

The invention claimed is:

1. A compound of formula (I)

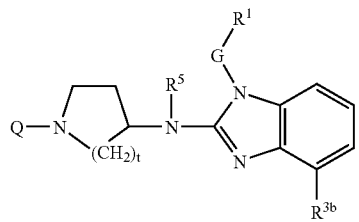

wherein

Q is $C_{1-6}$alkyl optionally substituted with one or more substituents each independently selected from the group consisting of trifluoromethyl, $C_{3-7}$cycloalkyl, Ar$^2$, hydroxy, $C_{1-4}$alkoxy, $C_{1-4}$alkylthio, Ar$^2$-oxy-, Ar$^2$-thio-, Ar$^2$(CH$_2$)$_n$oxy, Ar$^2$(CH$_2$)$_n$thio, hydroxycarbonyl, aminocarbonyl, $C_{1-4}$alkylcarbonyl, Ar$^2$carbonyl, $C_{1-4}$alkoxycarbonyl, Ar$^2$(CH$_2$)$_n$carbonyl, aminocarbonyloxy, $C_{1-4}$alkylcarbonyl-oxy, Ar$^2$-carbonyloxy, Ar$^2$(CH$_2$)$_n$carbonyloxy, $C_{1-4}$alkoxycarbonyl(CH$_2$)$_n$oxy, mono- or di($C_{1-4}$alkyl)aminocarbonyl, mono- or di($C_{1-4}$alkyl)aminocarbonyloxy, aminosulfonyl, mono- or di($C_{1-4}$alkyl)aminosulfonyl or a heterocycle selected from the group consisting of pyrrolidinyl, pyrrolyl, dihydropyrrolyl, imidazolyl, triazolyl, piperidinyl, homopiperidinyl, piperazinyl, pyridyl and tetrahydro-pyridyl, wherein each of said heterocycle may optionally be substituted with oxo or $C_{1-6}$alkyl; or Q is $C_{1-6}$alkyl substituted with two substituents wherein one substituent is selected from the group consisting of amino, mono- and di$C_{1-4}$alkyl-amino and Ar$^2$-$C_{1-4}$alkylamino and the other substituent is selected from the group consisting of carboxyl, $C_{1-6}$alkyloxycarbonyl, Ar$^2$-$C_{1-4}$alkyloxycarbonyl, aminocarbonyl and aminosulfonyl; wherein Ar$^2$ is phenyl or phenyl substituted with one substituent selected from the group consisting of halo, hydroxy, $C_{1-6}$alkyl, hydroxy$C_{1-6}$alkyl, polyhalo$C_{1-6}$alkyl, and $C_{1-6}$alkyloxy;

each n is independently 1, 2, 3, or 4;

t is 2;

G is methylene;

R$^{3b}$ is $C_{1-6}$alkyl;

R$^5$ is hydrogen; and

R1 is 3-hydroxy-6-methylpyrid-2-yl.

2. A compound according to claim 1, wherein R$^{3b}$ is methyl.

3. A compound according to claim 1 wherein Q is $C_{1-6}$alkyl optionally substituted with one or two substituents each independently selected from trifluoromethyl, $C_{3-7}$cycloalkyl, Ar$^2$, hydroxy, $C_{1-4}$alkoxy, Ar$^2$-oxy-, Ar$^2$(CH$_2$)$_n$oxy, hydroxycarbonyl, aminocarbonyl, $C_{1-4}$alkylcarbonyl, $C_{1-4}$alkoxy-carbonyl, aminocarbonyloxy, Ar$^2$(CH$_2$)$_n$carbonyloxy, $C_{1-4}$alkoxycarbonyl-(CH$_2$)$_n$oxy, mono- or di($C_{1-4}$alkyl)aminocarbonyl, aminosulfonyl, mono- or di($C_{1-4}$alkyl)aminosulfonyl or a heterocycle selected from pyrrolidinyl, pyrrolyl, dihydropyrrolyl, imidazolyl, triazolyl, piperidinyl, homopiperidinyl, piperazinyl and tetrahydropyridyl, wherein each of said heterocycle may optionally be substituted with oxo or $C_{1-6}$alkyl; or Q is $C_{1-6}$alkyl substituted with two substituents wherein one substituent is selected from amino and the other substituent is selected from the carboxyl and $C_{1-6}$alkyloxycarbonyl.

4. A compound according to claim 1 wherein Q is $C_{1-6}$alkyl optionally substituted with one or two substituents each independently selected from aminocarbonyl, $C_{1-4}$alkoxycarbonyl, aminocarbonyloxy, Ar$^2$(CH$_2$)$_n$carbonyloxy, mono- or di($C_{1-4}$alkyl)aminocarbonyl, aminosulfonyl, mono- or di($C_{1-4}$alkyl)aminosulfonyl, pyrrolidinyl, dihydropyrrolyl, piperidinyl, homopiperidinyl and tetrahydropyridyl; or Q is $C_{1-6}$alkyl substituted with two substituents wherein one substituent is amino and the other substituent is selected from carboxyl and $C_{1-6}$alkyloxycarbonyl.

5. A compound according to claim 1, wherein Q is $C_{1-6}$alkyl optionally substituted with one substituent selected from aminocarbonyl, $C_{1-4}$alkoxy-carbonyl, aminocarbonyloxy, Ar$^2$(CH$_2$)$_n$carbonyloxy, mono- or di($C_{1-4}$alkyl)-aminocarbonyl, aminosulfonyl, mono- or di($C_{1-4}$alkyl)aminosulfonyl, pyrrolidinyl, dihydropyrrolyl, piperidinyl, homopiperidinyl and tetrahydropyridyl, and optionally with a second substituent which is hydroxy or Q is $C_{1-6}$alkyl substituted with two substituents wherein one substituent is amino and the other substituent is selected from carboxyl and $C_{1-6}$alkyloxycarbonyl.

6. A compound according to claim 1, wherein Q is $C_{1-6}$alkyl substituted with aminocarbonyl, $C_{1-4}$alkoxycarbonyl, aminocarbonyloxy, mono- or di($C_{1-4}$alkyl)aminocarbonyl, aminosulfonyl, mono- or di($C_{1-4}$alkyl)aminosulfonyl, pyrrolidinyl, dihydropyrrolyl, piperidinyl, homopiperidinyl or tetrahydropyridyl.

7. A compound according to claim 1, wherein Q is

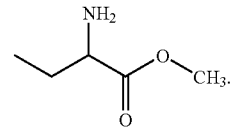

8. A compound according to claim 1, wherein Q is

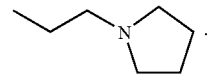

* * * * *